US011523983B2

(12) United States Patent
diZerega et al.

(10) Patent No.: US 11,523,983 B2
(45) Date of Patent: Dec. 13, 2022

(54) TREATMENT OF EPITHELIAL CYSTS BY INTRACYSTIC INJECTION OF ANTINEOPLASTIC PARTICLES

(71) Applicant: CRITITECH, INC., Lawrence, KS (US)

(72) Inventors: Gere S. diZerega, Lawrence, KS (US); Michael Baltezor, Lawrence, KS (US); Charles J. Decedue, Lawrence, KS (US); Sam Campbell, Lawrence, KS (US); Matthew McClorey, Lawrence, KS (US); Marc Iacobucci, Lawrence, KS (US); Holly Maulhardt, Lawrence, KS (US)

(73) Assignee: CritiTech, Inc., Lawrence, KS (US)

( * ) Notice: Subject to any disclaimer, the term of this patent is extended or adjusted under 35 U.S.C. 154(b) by 31 days.

(21) Appl. No.: 17/315,804

(22) Filed: May 10, 2021

(65) Prior Publication Data

US 2021/0259959 A1 Aug. 26, 2021

Related U.S. Application Data

(63) Continuation of application No. 16/382,446, filed on Apr. 12, 2019, now abandoned, which is a continuation of application No. PCT/US2018/036587, filed on Jun. 8, 2018.

(60) Provisional application No. 62/517,711, filed on Jun. 9, 2017.

(51) Int. Cl.
| | |
|---|---|
| A61K 9/10 | (2006.01) |
| A61K 9/00 | (2006.01) |
| A61P 35/00 | (2006.01) |
| A61B 8/08 | (2006.01) |
| A61B 8/12 | (2006.01) |
| A61K 9/107 | (2006.01) |
| A61K 9/14 | (2006.01) |
| A61K 31/337 | (2006.01) |
| A61K 47/26 | (2006.01) |
| A61P 1/18 | (2006.01) |
| A61K 9/16 | (2006.01) |

(52) U.S. Cl.
CPC .......... *A61K 9/0019* (2013.01); *A61B 8/0841* (2013.01); *A61B 8/12* (2013.01); *A61K 9/10* (2013.01); *A61K 9/107* (2013.01); *A61K 9/14* (2013.01); *A61K 31/337* (2013.01); *A61K 47/26* (2013.01); *A61P 1/18* (2018.01); *A61P 35/00* (2018.01); *A61K 9/1688* (2013.01)

(58) Field of Classification Search
None
See application file for complete search history.

(56) References Cited

U.S. PATENT DOCUMENTS

| | | |
|---|---|---|
| 5,399,363 A | 3/1995 | Liversidge et al. |
| 5,626,862 A | 5/1997 | Brem et al. |
| 5,833,891 A | 11/1998 | Subramaniam et al. |
| 5,874,029 A | 2/1999 | Subramaniam et al. |
| 5,874,481 A | 2/1999 | Weers et al. |
| 5,886,026 A | 3/1999 | Hunter et al. |
| 6,063,138 A | 5/2000 | Hanna et al. |
| 6,113,795 A | 9/2000 | Subramaniam et al. |
| 6,117,949 A | 9/2000 | Rathi et al. |
| 6,221,153 B1 | 4/2001 | Castor et al. |
| 6,348,209 B2 | 2/2002 | Placke et al. |
| 6,419,901 B2 | 7/2002 | Placke et al. |
| 6,562,952 B1 | 5/2003 | Rajewski et al. |
| 6,616,849 B1 | 9/2003 | Osajima et al. |
| 6,620,351 B2 | 9/2003 | Gupta et al. |
| 6,689,803 B2 | 2/2004 | Hunter |
| 6,749,868 B1 | 6/2004 | Desai et al. |
| 6,811,767 B1 | 11/2004 | Bosch et al. |
| 7,179,495 B1 | 2/2007 | Jan et al. |
| 7,208,106 B2 | 4/2007 | Shekunov et al. |
| 7,217,735 B1 | 5/2007 | Au et al. |
| 7,276,190 B2 | 10/2007 | Reverchon |
| RE40,493 E | 9/2008 | Straub et al. |
| 7,455,797 B2 | 11/2008 | Shekunov et al. |
| 7,556,798 B2 | 7/2009 | Edwards et al. |
| 7,566,436 B2 | 7/2009 | Lester et al. |
| 7,744,923 B2 | 6/2010 | Rajewski et al. |
| 7,754,777 B2 | 7/2010 | Ventosa et al. |
| 7,820,788 B2 | 10/2010 | Desai et al. |
| 7,829,598 B2 | 11/2010 | Iversen et al. |
| 7,833,444 B2 | 11/2010 | Watano |
| 8,043,631 B2 | 10/2011 | Au et al. |
| 8,138,229 B2 | 3/2012 | Desai et al. |
| 8,221,779 B2 | 7/2012 | Jonas et al. |
| 8,314,156 B2 | 11/2012 | Desai et al. |
| 8,735,394 B2 | 5/2014 | Desai et al. |
| 8,778,181 B1 | 7/2014 | Johnson et al. |

(Continued)

FOREIGN PATENT DOCUMENTS

| | | |
|---|---|---|
| CN | 1463969 | 12/2003 |
| CN | 1923189 A | 3/2007 |

(Continued)

OTHER PUBLICATIONS

U.S. Appl. No. 16/669,310, filed Oct. 30, 2019, Crititech, Inc.
U.S. Appl. No. 16/669,692, filed Oct. 31, 2019, Crititech, Inc.
U.S. Appl. No. 16/714,151, filed Dec. 13, 2019, Crititech, Inc.
U.S. Appl. No. 16/714,099, filed Dec. 13, 2019, Crititech, Inc.
U.S. Appl. No. 16/776,919, filed Jan. 30, 2020, Crititech, Inc.
U.S. Appl. No. 16/834,155, filed Mar. 30, 2020, Crititech, Inc.

(Continued)

*Primary Examiner* — Jessica Worsham
(74) *Attorney, Agent, or Firm* — McDonnell Boehnen Hulbert & Berghoff LLP

(57) ABSTRACT

Disclosed herein are methods for treating epithelial cysts, including pancreatic cysts, in a subject by intracystic injection of compositions comprising antineoplastic particles, including taxane particles such as paclitaxel particles and docetaxel particles.

18 Claims, 3 Drawing Sheets

(56) References Cited

U.S. PATENT DOCUMENTS

| | | | |
|---|---|---|---|
| 8,906,392 | B2 | 12/2014 | Berkland et al. |
| 9,233,348 | B2 | 1/2016 | Johnson et al. |
| 9,278,069 | B2 | 3/2016 | Berkland et al. |
| 9,301,926 | B2 | 4/2016 | Indolfi et al. |
| 9,339,554 | B2 | 5/2016 | Rijcken et al. |
| 9,511,046 | B2 | 12/2016 | Desai et al. |
| 9,617,338 | B1 | 4/2017 | Campbell et al. |
| 9,763,946 | B2 | 9/2017 | Lin |
| 9,814,685 | B2 | 11/2017 | Baltezor et al. |
| 9,895,197 | B2 | 2/2018 | Poquet et al. |
| 9,918,957 | B2 | 3/2018 | Baltezor et al. |
| 10,391,090 | B2 | 8/2019 | Baltezor et al. |
| 10,398,646 | B2 | 9/2019 | Baltezor et al. |
| 10,507,181 | B2 | 12/2019 | Baltezor et al. |
| 10,507,195 | B2 | 12/2019 | Baltezor et al. |
| 10,729,673 | B2 | 8/2020 | Baltezor et al. |
| 10,874,660 | B2 | 12/2020 | Baltezor et al. |
| 10,894,045 | B2 | 1/2021 | Baltezor et al. |
| 2001/0029264 | A1 | 10/2001 | McChesney-Harris |
| 2002/0081339 | A1 | 6/2002 | Menei et al. |
| 2002/0102294 | A1 | 8/2002 | Bosch et al. |
| 2003/0166509 | A1 | 9/2003 | Edwards et al. |
| 2003/0190284 | A1 | 10/2003 | Annapragada et al. |
| 2004/0033267 | A1 | 2/2004 | Merisko-Liversidge et al. |
| 2004/0092577 | A1 | 5/2004 | Lerner et al. |
| 2004/0220081 | A1 | 11/2004 | Kreitz et al. |
| 2005/0059613 | A1 | 3/2005 | Memarzadeh et al. |
| 2005/0131057 | A1 | 6/2005 | Uneo et al. |
| 2005/0238725 | A1 | 10/2005 | Cunningham et al. |
| 2006/0034925 | A1 | 2/2006 | Au |
| 2006/0078619 | A1 | 4/2006 | Woo et al. |
| 2006/0127420 | A1 | 6/2006 | Chung et al. |
| 2006/0147535 | A1 | 7/2006 | Muthukumaran et al. |
| 2006/0188566 | A1 | 8/2006 | Liversidge et al. |
| 2008/0063699 | A1 | 3/2008 | Teifel et al. |
| 2008/0089944 | A1 | 4/2008 | Rajewski et al. |
| 2008/0160095 | A1 | 7/2008 | Desai et al. |
| 2009/0215882 | A1 | 8/2009 | Bouzada et al. |
| 2010/0197944 | A1 | 8/2010 | Palle et al. |
| 2011/0223203 | A1 | 9/2011 | Berkland et al. |
| 2011/0293672 | A1 | 12/2011 | Lewis et al. |
| 2012/0087984 | A1 | 4/2012 | Liversidge et al. |
| 2012/0177910 | A1 | 7/2012 | Weber et al. |
| 2012/0237768 | A1 | 9/2012 | Hirokawa et al. |
| 2012/0321698 | A1 | 12/2012 | Narain et al. |
| 2014/0038931 | A1 | 2/2014 | Hirokawa et al. |
| 2014/0079782 | A1 | 3/2014 | York et al. |
| 2014/0154269 | A1 | 6/2014 | Tour et al. |
| 2014/0199244 | A1 | 7/2014 | Rijcken et al. |
| 2014/0243364 | A1 | 8/2014 | Agisim et al. |
| 2014/0294967 | A1 | 10/2014 | Borbely et al. |
| 2015/0037252 | A1 | 2/2015 | Hawkett et al. |
| 2015/0118311 | A1 | 4/2015 | Zhou et al. |
| 2015/0342872 | A1 | 12/2015 | Williamson et al. |
| 2015/0375153 | A1 | 12/2015 | Johnson et al. |
| 2016/0257752 | A1 | 9/2016 | Kim et al. |
| 2016/0263232 | A1 | 9/2016 | Amighi et al. |
| 2016/0339090 | A1 | 11/2016 | Hacohen et al. |
| 2016/0354336 | A1 | 12/2016 | Baltezor et al. |
| 2016/0362658 | A1 | 12/2016 | Leen et al. |
| 2016/0374953 | A1 | 12/2016 | Baltezor et al. |
| 2017/0119881 | A1 | 5/2017 | Saha et al. |
| 2018/0169058 | A1 | 6/2018 | Baltezor et al. |
| 2018/0177739 | A1 | 6/2018 | Johnson et al. |
| 2018/0306748 | A1 | 10/2018 | Seuthe |
| 2018/0360748 | A1 | 12/2018 | Baltezor et al. |
| 2019/0127803 | A1 | 5/2019 | Hacohen et al. |
| 2019/0151478 | A1 | 5/2019 | Valton et al. |
| 2019/0343824 | A1 | 11/2019 | Baltezor et al. |
| 2020/0246326 | A1 | 8/2020 | Baltezor et al. |
| 2020/0405684 | A1 | 12/2020 | Baltezor et al. |
| 2021/0000786 | A1 | 1/2021 | Baltezor et al. |

FOREIGN PATENT DOCUMENTS

| | | |
|---|---|---|
| CN | 101129338 | 2/2008 |
| CN | 101336899 A | 1/2009 |
| CN | 101829061 | 9/2010 |
| CN | 102488682 A | 6/2012 |
| CN | 107281502 A | 10/2017 |
| EP | 3 181 123 | 6/2017 |
| JP | H11279052 | 10/1999 |
| PT | 104693 A | 1/2011 |
| TW | 201408304 A | 3/2014 |
| WO | 2000/57852 | 10/2000 |
| WO | WO 00/72827 | 12/2000 |
| WO | 2001/36007 A2 | 5/2001 |
| WO | 2002/087563 A2 | 11/2002 |
| WO | 2003/030941 | 4/2003 |
| WO | WO 03/032906 | 4/2003 |
| WO | 2003/090722 A2 | 11/2003 |
| WO | WO 03/090715 | 11/2003 |
| WO | 2004/009076 A1 | 1/2004 |
| WO | 2004/089291 A2 | 10/2004 |
| WO | WO 2005/025542 | 3/2005 |
| WO | 2006/068890 A2 | 6/2006 |
| WO | 2006/099385 A2 | 9/2006 |
| WO | WO 2006/103112 | 10/2006 |
| WO | 2007/027941 | 3/2007 |
| WO | 2007/027941 A2 | 3/2007 |
| WO | WO 2007/104549 | 9/2007 |
| WO | WO 2008/137148 | 11/2008 |
| WO | 2009/111271 A1 | 9/2009 |
| WO | 2011/153009 A1 | 12/2011 |
| WO | WO 2012/051426 | 4/2012 |
| WO | 2015/103005 | 7/2015 |
| WO | WO 2015/187194 | 12/2015 |
| WO | 2016/197091 | 12/2016 |
| WO | 2017/049083 A2 | 3/2017 |
| WO | 2017/053920 | 3/2017 |
| WO | 2017/127729 | 7/2017 |
| WO | 2017/176628 | 10/2017 |
| WO | 2017/176628 | 12/2017 |
| WO | WO 2018/045239 | 3/2018 |
| WO | WO 2018/170196 | 9/2018 |
| WO | WO 2018/170207 | 9/2018 |
| WO | WO 2018/170210 | 9/2018 |
| WO | WO 2018/227037 | 12/2018 |
| WO | WO 2018/231908 | 12/2018 |

OTHER PUBLICATIONS

U.S. Appl. No. 16/839,737, filed Apr. 3, 2020, Crititech, Inc.
US 10,624,886, 08/2019, Baltezor et al. (withdrawn)
Carson et al. "Cellular immunity in breast cancer patients completing taxane treatment" Clinical Cancer Research 10:3401-09 (May 2004).
Ma et al., "Effective antitumor activity of paclitaxel-loaded poly (epsiloncaprolactone)/pluronic F68 nanoparticles after intratumoral delivery into the murine breast cancer model," Anti-Cancer Drugs, 21(3):261-69 (2010).
Roby et al., "Syngeneic mouse model of epithelial ovarian cancer: effects of nanoparticulate paclitaxel, Nanotax®," Advances in Experimental Medicine and Biology, 622:169-81 (2008).
Saloustros et al., (Expert Opin. Pharmacother. (2008) 9(15):2603-2616) (Year: 2008).
Socinski et al. (Current Oncology, vol. 21, No. 5, Oct. 2014, pp. e691-e703 (Year: 2014).
Zheng et al., "Enhanced antitumor efficiency of docetaxel-loaded nanoparticles in a human ovarian xenograft model with lower systemic toxicities by intratumoral delivery," Oncology Reports, 23(3):717-24 (2010).
Amiji et al. "Intratumoral Administration of Paclitaxel in an In Situ Gelling Poloxamer 407 Formulation," Pharmaceutical Development and Technology, 7(2), 129-202 (2002).
Anastasiadis et. al. "Best practice in the treatment of nonmuscle invasive bladder cancer" Ther Adv Urol (2012) 4(1) 13-32.
Arnone et al. "Commentary: Current status of intratumoral therapy for glioblastoma," J Neurol Neuromed (2016) 1(6): 27-31.

(56) References Cited

OTHER PUBLICATIONS

Asmawi et al. "Excipient selection and aerodynamic characterization of nebulized lipid-based nanoemulsion loaded with docetaxel for lung cancer treatment", Drug Delivery and Translational Research, vol. 9, No. 2, Apr. 2018, pp. 543-554.
Axiak-Bechtel et al. "Nanoparticulate paclitaxel demonstrates antitumor activity in PC3 and Ace-1 aggressive prostate cancer cell lines," Invest New Drugs 2013;31:1609-1615.
Barura, et al "Challenges associated with penetration of nanoparticles across cell and tissue barriers: A review of current status and future prospects," Nano Today, 9: 223-243, 2014.
Bilusic et. al. "Immunotherapy of Prostate Cancer: Facts and Hopes", Clin Cancer Res; 23(22); 6764-70, 2017.
Bouquet, et al., "Drug Delivery of paclitaxel for an intraperitoneal chemotherapy," Thesis, 2009.
Bracci et al. "Immune-Based mechanisms of cytotoxic chemotherapy: implications for the design of novel and rationale-Based combined treatments against cancer." Cell Death and Differentiation, vol. 21, No. 1, 2013, pp. 15-25., doi:10.1038/cdd.2013.67.
Buda et. al. "Randomised controlled trial comparing single agent paclitaxel vs epidoxorubicin plus paclitaxel in patients with advanced ovarian cancer in early progression after platinum-based chemotherapy", British Journal of Cancer (2004) 90, 2112-2117.
Butterfield "Cancer vaccines" BMJ. 2015; 350; h988.
Cao et. al. "Tumor associated macrophages and angiogenesis dual-recognizable nanoparticles for enhanced cancer chemotherapy" Nanomedicine: Nanotechnology, Biology, and Medicine 14 (2018) 651-659.
Carbone, et al "Non-Small Cell Lung Cancer: Role of the Immune System and Potential for Immunotherapy," J Thorac Oncol, 10(7): 974-984, 2015.
Castellanos, "The relationship between attractive interparticles forces and bulk behaviors in dry and uncharged fine powders," Advances in Physics, 54(4): 263-376, 2005.
Celegene "What is the optimal chemotherapy partner for immune checkpoint inhibitor drugs?" Presentation Mar. 16, 2017 by Eric Raymond at Mediterranean Institute for Life Sciences, Republic of Croatia, 73 pages.
Chan et. al. "The immunological effects of taxanes". Cancer Immunol. Immunother. Jul. 2000;49(4-5):181-5.
Charoenchaitrakool, et al., "Micronization by Rapid Expansion of Supercritical Solutions to Enhance the Dissolution Rates of Poorly Water-Soluble Pharmaceuticals," Ind Eng Chem Res, 2000, 39: 4794-4802.
Chen et. al. "Chemoimmunotherapy: reengineering tumor immunity". Cancer Immunol. Immunother. 62, 203-216, 2013.
clintrials.gov "A study of Pembrolizumab (MK-3475) in combination with chemotherapy or immunotherapy in participants with lung cancer" Jan. 16, 2014.
Colbeck et. al. "Tertiary Lymphoid Structures in Cancer: Drivers of Antitumor Immunity, Immunosuppression, or Bystander Sentinels in Disease?" Front Immunol, 8, 1830. doi:10.3389/fimmu.2017.01830.
Crown et al., "Docetaxel and Paclitaxel in the treatment of breast cancer: A review of clinical experience," The Oncologist (2004) vol. 9(2), pp. 24-32.
Della Porta and Reverchon, "Engineering Powder Properties by supercritical fluid for optimum Drug Delivery, Part One: Supercritical Antisolvent Precipitation," BioProcessTechnical, Feb. 2005, 48-52.
Della Porta and Reverchon, Engineering Powder Properties by supercritical fluid for optimum Drug Delivery, Part Two: Supercritical Assisted Atomization, BioProcess Technical, Mar. 2005, 54-60.
Deng et al. "Understanding the Structure and Stability of Paclitaxel nanocrystals," Int J Pharm May 10, 2010, 390(2): 242-249.
Desai et al. "Improved effectiveness of nanoparticle albumin-bound (nab) paclitaxel versus polysorbate-based docetaxel in multiple xenografts as a function of HER2 and SPARC status," Anti-Cancer Drugs 2008, 19:899-909.

Desai et al. "Increased Antitumor Activity, Intratumor Paclitaxel Concentrations, and Endothelial Cell Transport of Cremophor-Free, Albumin-Bound Paclitaxel, ABI-007, Compared with Cremophor-Based Paclitaxel," Clin Cancer Res 2006;12(4).
Desai, et al, "Pulmonary delivery of a novel, cremophor-free, protein-based nanoparticle preparation of paclitaxel," Proceedings of the American Association for Cancer Research, 44: 731-732, Abstract 2003.
Diaz et al. "Concomitant combination of active immunotherapy and carboplatin-or paclitaxel-based chemotherapy improves anti-tumor response." Cancer Immunology, Immunotherapy 62.3 (2013): 455-469.
Eisenhauer et. al. "New response evaluation criteria in solid tumours: Revised RECIST guideline (version 1.1)" European Jounral of Cancer 45 (2009) 228-247.
Elstad et al. "OncoGel (ReGel/paclitaxel)—Clinical applications for a novel paclitaxel delivery system," Advanced Drug Delivery Reviews 61 (2009) 785-794.
Engels et al. "Alternative drug formulations of docetaxel: a review," Anti-Cancer Drugs 2007 18:95-103.
Feng et al. "A critical review of lipid-based nanoparticles for taxane delivery," Cancer Letters 334 (2013) 157-175.
Ferenbach et. al. "Macrophages and dendritic cells: what is the difference?" Kidney International (2008) 74.
Finkelstein et. al. "Serial assessment of lymphocytes and apoptosis in the prostate during coordinated intraprostatic dendritic cell injection and radiotherapy" Immunotherapy (2012) 4 (4), 373-382.
Forde et. al. "Neoadjuvant PD-1 Blockade in Resectable Lung Cancer" N Engl J Med 2018; 378;1976-86.
Gajewski "Fast Forward—Neoadjuvant Cancer Immunotherapy" N Engl J Med 378;21, May 24, 2018, 2034-35.
Galluzzi et. al. The secret ally: immunostimulation by anticancer drugs. Nat. Rev. Drug Discov. 11, 215-233, 2012.
Garnett et. al. "Combination of docetaxel and recombinant vaccine enhances T-cell responses and antitumor activity: effects of docetaxel on immune enhancement." Clinical Cancer Research 14.11 (2008): 3536-3544.
Ghosh et al. "Nanosuspensions for improving the bioavailability of a poorly soluble drug and screening of stabilizing agents to inhibit crystal growth," International Journal of Pharmaceutics 409 (2011) 260-268.
Goldberg et al. "Intratumoral cancer chemotherapy and immunotherapy: opportunities for nonsystemic preoperative drug delivery," JPP 2002, 54: 159-180.
Govindan et al. "Phase III trial of ipilimumab combined with paclitaxel and carboplatin in advanced squamous non-small-cell lung cancer." Journal of Clinical Oncology (2017): JCO-2016.
Gruden et al., "Antitumoral effect and reduced systemic toxicity in mice after intra-tumoral injection of an in vivo solidifying calcium sulfate formulation with docetaxel", European Journal of Pharmaceutics and Biopharmaceutics, 114 (2017); 186-193.
Grünwald et al. "The role of nephrectomy in metastatic renal cell carcinoma" Nature Reviews Nephrology 14(10):601-602 (Oct. 2018).
Gu et al. "Nanoformulation of paclitaxel to enhance cancer therapy," Journal of Biomaterials Applications 28(2) 198-307 2012.
Gulley et. al. "Phase I study of intraprostatic vaccine administration in men with locally recurrent or progressive prostate cancer". Cancer Immunol Immunother, 2013;62,1521-1531.
Hershey, et al, "Inhalation Chemotherapy for Macroscopic Primary or Metastatic Lung Tumors: Proof of Principle Using Dogs with Spontaneously Occurring Tumors as a Model," Clinical Cancer Research, 5:2653-2659, 1999.
Hiraoka, et al, "Concurrent infiltration by CD8+T cells and CD4+T cells is a favourable prognostic factor in non-small-cell lung carcinoma," British Journal of Cancer, 94: 275-280, 2006.
Hohenforst-Schmidt, "Intratumoral chemotherapy for lung cancer: re-challenge current targeted therapies," Drug Design, Development and Therapy, 571-583, 2013.
Hussain et al. "Long-term follow-up of a prospective trial of trimodality therapy of weekly paclitaxel, radiation, and androgen deprivation in high-risk prostate cancer with or without prior prostatectomy," Int J Radiation Oncology Biol Phys. 2012;82(1):167-174.

(56) References Cited

OTHER PUBLICATIONS

"Inman, ""Atezolizumab/Nab-Paclitaxel Combo Shows High Response Rates in TNBC"". Internet Citation. Dec. 10, 2015. Retrieved from the Internet:URL:http://www.onclive.comjconference-coverage/sabcs-2015/atezolizumab-nab-paclitaxel-combo-shows-high-response-rates-in-tnbc [retrieved Oct. 20, 2017]."
Atar et al. "EUS Guided Injection of Albumin Bound Paclitaxel Into Mucinous Pancreatic Cysts," Gastrointestinal Endoscopy, vol. 81, No. 5S : 2015.
Choi et al. "Long-term outcomes after endoscopic ultrasound-guided ablation of pancreatic cysts," Endoscopy, 2017; 49: 866-873.
Dewitt et al. "Alteration in cyst fluid genetics following endoscopic ultrasound-guided pancreatic cyst ablation with ethanol and paclitaxel," Endoscopy 2014; 46(06): 457-464.
Dewitt "Pancreatic cyst ablation: why are we not doing more of these procedures?" Endoscopy, 2017; 49: 839-841.
Farrell et al. "Pancreatic Cystic Neoplasms: Management and Unanswered Questions," Gastroenterology 2013;144:1303-1315.
Farrell "Prevalence, Diagnosis and Management of Pancreatic Cystic Neoplasms: Current Status and Future Direction," Gut and Liver, vol. 9, No. 5, Sep. 2015, pp. 571-589.
Gomez et al. "EUS-guided ethanol lavage does not reliably ablate pancreatic cystic neoplasms," Gastrointestinal Endoscopy vol. 83, No. 5 : 2016.
Hosein et al. "A Phase II Trial of nab-Paclitaxel as Second-line Therapy in Patients with Advanced Pancreatic Cancer," American Journal of Clinical Oncology, vol. 36, No. 2, Apr. 2013.
Indolfi et al. "A tunable delivery platform to provide local chemotherapy for pancreatic ductal adenocarcinoma," Biomaterials, 2016;93:71-82.
Linghu et al. "Feasibility of Endoscopic Ultrasound-Guided OncoGel (ReGel/Paclitaxel) Injection into the Pancreas in Pigs," Endoscopy 2005; 37 (11): 1140-1142.
Matthes et al. "EUS-guided injection of paclitaxel (OncoGel) provides therapeutic drug concentrations in the porcine pancreas," Gastrointest Endosc. 2007;65(3):448-453.
McGrath "Management of incidental pancreatic cysts: which guidelines?" Endoscopy International Open 2017; 05: E209-E211.
Mills et al. "Possible Drug-Associated Pancreatitis after Paclitaxel-Cremophor Administration," Pharmacotherapy: The Journal of Human Pharmacology and Drug Therapy, vol. 20, Issue 1, Jan. 2000, pp. 95-97.
Moyer et al. "Is alcohol required for the effective pancreatic cyst ablation? The prospective randomized CHARM trial pilot study," Endoscopy International Open, 2016; 04: E603-E607.
Oh et al. "New treatment for cystic tumors of the pancreas: EUS-guided ethanol lavage with paclitaxel injection," Gastrointest Endosc. 2008;67(4):636-642.
Oh et al. "Endoscopic Ultrasonography-Guided Ethanol Lavage with Paclitaxel Injection Treats Patients with Pancreatic Cysts," Gastroenterology 2011;140:172-179.
Pitman et al. "Pancreatic Cysts Preoperative Diagnosis and Clinical Management," Cancer Cytopathology, Feb. 25, 2010, pp. 1-13, published online Dec. 30, 2009.
Sarr et al. "Cystic Neoplasms of the Pancreas: Benign to Malignant Epithelial Neoplasms," Surgical Clinics of North America, vol. 81, Issue 3, Jun. 1, 2001, pp. 497-509.
Stark et al. "Pancreatic Cyst Disease A Review," JAMA May 3, 2016 vol. 315, No. 17.
Tanaka et al. "Clinical aspects of intraductal papillary mucinous neoplasm of the pancreas," J Gastroenterol 2005; 40:669-675.
Tanaka et al. "International consensus guidelines 2012 for the management of IPMN and MCN of the pancreas," Pacreatology 12 (2012) 183-197.
Tanaka "Current best practice and controversies in the follow up of patients with asymptomatic branch duct IPMN of the pancreas," HPB 2016, 18, 709-711.
Zhang et al. "Endoscopic ultrasound-guided ethanol ablation therapy for tumors," World J Gastroenterol Jun. 14, 2013; 19(22): 3397-3403.
Ranade et al. "Clinical and economic implications of the us of nanoparticle paclitaxel (Nanoxel) in India," Annals of Oncology 24 (Supplement 5): v6-v12, 2013.
Rasenack, et al., Micronization of Anti-Inflammatory Drugs for Pulmonary Delivery by a Controlled Crystallization Process, J Pharm Sci, 92:35-44, 2003.
Ruel-Gariepy et al. "A thermosensitive chitosan-based hydrogel for the local delivery of paclitaxel," European Journal of Pharmaceutics and Biopharmaceutics 57 (2004) 53-63.
Saltus "Enhancing Immunotherapy: The Race to Make Cold Tumors Hot" published online on Apr. 27, 2018 at https://www.dana-farber.org/newsroom/publications/paths-of-progress-2018/enhancing-immunotherapy/.
Sanfilippo et al. "Phase I/II study of biweekly paclitaxel and radiation in androgen-ablated locally advanced prostate cancer," J Clin Oncol. 2008;26(18):2973-2978.
Sautes-Fridman et. al. "Tertiary Lymphoid Structures in Cancers: Prognostic Value, Regulation, and Manipulation for Therapeutic Intervention" Front. Immunol. 7;407, 2016.
Schumacher et. al. "Neoantigens in cancer immunotherapy" Science vol. 348, Issue 6230, Apr. 3, 2015.
Sevko Antitumor effect of paclitaxel is mediated by inhibition of myeloid-derived suppressor cells and chronic inflammation in the spontaneous melanoma model. J. Immunol. 190,2464-2471 (2013).
Sevko et al. Application of paclitaxel in low non-cytotoxic doses supports vaccination with melanoma antigens in normal mice. J Immunotoxicol. Jul.-Sep. 2012;9(3):275-81.
Sharma, et al., "Development of Stabilized Paclitaxel nanocrystals: In vitro and in vivo efficacy studies," European Jounral of Pharmaceuticals Science, 69: 51-60, Jan. 2015.
Shepard et al. "Phase II trial of neoadjuvant nab-paclitaxel in high risk patients with prostate cancer undergoing radical prostatectomy," J Urol. 2009;181:1672-1677.
Shi et. al. "PD-1 Blockade Boosts Radiofrequency Ablation-Elicited Adaptive Immune Responses against Tumor" Clin. Cancer Res; 22(5); 1179-84, 2016.
Shurin et al. "Cancer Therapy and Dendritic Cell Immunomodulation," Chapter 14, Dendritic Cells in Cancer, Shurin et al. (eds.) Springer Science+Business Media, LLC 2009.
Slovin "Chemotherapy and immunotherapy combination in advanced prostate cancer." Clin Adv Hematol Oncol 10.2 (2012): 90-100.
Snavely, et al., "Micronization of insulin from halogenated alcohol solution using supercritical carbon dioxide as an antisolvent," J Pharm Sci, 91:2026-2039, 2002.
Soliman "nab-Paclitaxel as a potential partner with checkpoint inhibitors in solid tumors" Onco Targets and Therapy 10:101-112 (Dec. 2016).
Surapaneni et al. "Designing Paclitaxel Drug Delivery Systems Aimed at Improved Patient Outcomes: Current Status and Challenges," ISRN Pharmacology, vol. 2012, Article ID 623139, 2012.
Swartz et al. "Lymphatic and interstitial flow in the tumor microenvironment: linking mechanobiology with immunity," Nature Reviews Cancer, vol. 12, Mar. 2012.
Van Soest et al. "Irrefutable evidence for the use of docetaxel in newly diagnosed metastatic prostate cancer: results from the STAMPEDE and CHAARTED trials," BMC Medicine (2015) 13:304.
Vanneman et. al. Combining immunotherapy and targeted therapies in cancer treatment. Nat. Rev. Cancer 12, 237-251, 2012.
Vaz-Luis et. al. "Survival Benefit Needed to Undergo Chemotherapy: Patient and Physician Preferences" Cancer Aug. 1, 2017, 2821-2828, published online Mar. 21, 2017 in Wiley Online Library (wileyonlinelibrary.com).
Vemavarapu, Particle formation by rapid expansion of supercritical solutions, Dissertation 2002.
Vukelja et al. "Phase 1 study of escalating-dose OncoGel (ReGel/paclitaxel) depot injection, a controlled-release formulation of paclitaxel, for local management of superficial solid tumor lesions. Anticancer Drugs," 2007; 18(3): 283-9.
Wakabayashi, et al, "CD4+ T cells in cancer stroma, not CD8+ T cells in cancer cell nests, are associated with favorable prognosis in human non-small cell lung cancers," Cancer Sci, 94(11): 1003-1009, Nov. 2003.

(56) References Cited

OTHER PUBLICATIONS

Wang et al. "Intratumoral Injection of Taxol In Vivo Suppresses A549 Tumor Showing Cytoplasmic Vacuolization," Journal of Cellular Biochemistry 113:1397-1406 (2012).
Weiss et al. "A phase Ib study of pembrolizumab plus chemotherapy in patients with advanced cancer (PembroPlus)." British Journal of Cancer (2017).
Werth, et al., "Agglomeration of Charged Nanopowders in Suspensions," Phys Rev E Stat Nonlin Soft Matter Phys. Feb. 2006;73(2 Pt 1):021402. Epub Feb. 10, 2006.
Williamson, et al., "Phase I clinical trial of the intraperitoneal (IP) administration of a novel nanoparticle formulation of paclitaxel (NTX)," Poster Presentation, ACS, Sep. 2013.
Worley et. al. "Docetaxel accumulates in lymphatic circulation following subcutaneous delivery compared to intravenous delivery in Rats" Anticancer Research 36; 5071-5078 (2016).
Wu et al. "Physical and chemical stability of drug nanoparticles," Advanced Drug Delivery Reviews 63 (2011) 456-469.
Wysham et al. "Adding bevacizumab to single agent chemotherapy for the treatment of platinum-resistant recurrent ovarian cancer: A cost effectiveness analysis of the AURELIA trial" Gynecologic Oncology 145 (2017) 340-345.
Xing, et al., "Efficacy and safety of albumin-bound paclitaxel in treating recurrent advanced non-small-cell lung cancer," Chinese Journal of Cancer Research, 25(2):200-205, 2013.
Yoo et al. "An In Vivo Evaluation of Docetaxel Delivered Intratumorally in Head and Neck Squamous Cell Carcinoma," Arch Otolaryngol Head Neck Surg/vol. 131, May 2005.
Young, Characterisation of particle-particles interactions using the atomic force microscope, Dissertation, 2002.
Yu et al. "Tumor-immune profiling of murine syngeneic tumor models as a framework to guide mechanistic studies and predict therapy response in distinct tumor microenvironments," PLOS One https://doi.org/10.1371/journal.pone.0206223 Nov. 2, 2018.
Zarogoulidis, et al, "Inhaled chemotherapy in lung cancer: future concept of nanomedicine," International Journal of Nanomedicine, 7: 1551-1572, Mar. 2012.
Zentner et al. "Biodegradable block copolymers for delivery of proteins and water-insoluble drugs," Journal of Controlled Release 91 (2001) 203-215.
Zhang et. al. MTDH/AEG-1 based DNA vaccine suppresses metastasis and enhances chemosensitivity to paclitaxel in pelvic lymph node metastasis Biomedicine & Pharmacotherapy 70 (2015) 217-226.
Zhao et al. "Preparation of superparamagnetic paclitaxel nanoparticles from modified chitosan and their cytotoxicity against malignant brain glioma," English Abstract, Journal of Biomedical Engineering Jun. 1, 2011, 28(3):513-516 (lang: chi).
Zhao et. al. "New Avenues for Nanoparticle-Related Therapies" Nanoscale Research Letters (2018) 13;136.
Zheng et. al. "Chemotherapy-induced immunomodulation in non-small-cell lung cancer: a rationale for combination chemoimmunotherapy" Immunotherapy (2017) 9(11), 913-927.
Zhou et al. "Highly penetrative, drub-loaded nanocarriers improve treatment of glioblastoma," PNAS, Jul. 16, 2013, vol. 110, No. 29, 11751-11756.
Zhou, "Atomized paclitaxel liposome inhalation treatment of bleomycin-induced pulmonary fibrosis in rats," Genetics and Molecular Research, 15(2): 1-11, 2016.
Zitvogel et. al. "Mechanism of action of conventional and targeted anticancer therapies: reinstating immunosurveillance." Immunity 39.1 (2013): 74-88.
Jackson et al. "The Suppression of Human Prostate Tumor Growth in Mice by the Intratumoral Injection of a Slow-Release Polymeric Paste Formulation of Paclitaxel," Cancer Research 60, 4146-4151, Aug. 1, 2000.
Janeway et al. "Using the immune response to attack tumors," Immunobiology: The Immune System in Health and Disease, 5th ed, New York: Garland Science; 2001.
Javeed et. al. Paclitaxel and immune system. Eur J Pharm Sci. Nov. 5, 2009;38(4):283-90.
Johnston, et al., "Nanotax Injectable Nanocystal Paclitaxel for Ovarian and Other Intraperitoneal Cancers," Datasheet, Sep. 2013.
Kakran Mitali, et al., "Modified supercritical antisolvent method with enhanced mass transfer to fabricate drug nanoparticles," Materials Science and Engineering, 33(5): 2864-2870, Mar. 2013.
Kalos et al. "T Cells with Chimeric Antigen Receptors Have Potent Antitumor Effects and Can Establish Memory in Patients with Advanced Leukemia," Sci Transl Med. Aug. 10, 2011; 3(95) 95ra73.
Khullar et al. "Nanoparticle Migration and Delivery of Paclitaxel to Regional Lymph Nodes in a Larch Animal Model," J Am Coll Surg. Mar. 2012; 214(3): 328-337.
Koay et al. "Intra-tumoral heterogeneity of gemcitabine delivery and mass transport in human pancreatic cancer," Phys Biol.; 11(6): 065002 2015.
Kodumudi et. al. A novel chemoimmunomodulating property of docetaxel: suppression of myeloid-derived suppressor cells in tumor bearers. Clin. Cancer Res 16, 4583-4594, 2010.
Koshkina, et al, "Cyclosporin A Aerosol Improves the Anticancer Effect of Paclitaxel Aerosol in Mice," Journal of Aerosol Medicine, 17(1): 7-14, 2004.
Koshkina, et al, "Improved respiratory delivery of the anticancer drugs, camptothecin and paclitaxel, with 5% $CO_2$-enriched air: pharmacokinetic studies," Cancer Chemother Pharmacol, 47:451-456, Oct. 2001.
Kulkarni, et al, "The Use of Systemic Treatment in the Maintenance of Patients with Non-Small Cell Lung Cancer: A Systematic Review," Journal of Thoracic Oncology, 11(7): 989-1002, 2016.
Lapidus et al. "Anti-tumor effect of combination therapy with intratumoral controlled-release paclitaxel (PACLIMER® Microspheres) and radiation," Prostate. 2004;58:291-298.
Lee et al. "In vivo efficacy of paclitaxel-loaded injectable in situ-forming gel against subcutaneous tumor growth," International Journal of Pharmaceutics 392 (2010) 51-56.
Lee, et al., "Supercritical antisolvent production of biodegradable micro-and nanoparticles for controlled delivery of paclitaxel," Journal of Controlled Release, 125(2): 96-106, Oct. 2007.
Lee et al, "Macrophage-Based Cell Therapies: The Long and Winding Road," J Control Release. Oct. 28, 2016; 240: 527-540.
Liu et. al. Pre-treatment with chemotherapy can enhance the antigenicity and immunogenicity of tumours by promoting adaptive immune responses. Br. J. Cancer 102, 115-123, 2010.
Liu, et al, "Enabling Anticancer Therapeutics by Nanoparticle Carriers: The Delivery of Paclitaxel," Int J. Mol. Sci., 12:4395-4413, 2011.
Liu, et al, "Paclitaxel Nanocrystals for Overcoming Multidrug Resistance in Cancer," Mol Pharm, 7(3): 863-869, 2010.
Lu et. al. "Paclitaxel-loaded gelatin nanoparticle for intravesical bladder cancer therapy" Clinical Cancer Research vol. 10, Issue 22, Nov. 2004.
Lu et. al. "Paclitaxel Gelatin nanoparticles for Intravesical Bladder Cancer Therapy" The Journal of Urology vol. 185, 1478-1483, Apr. 2011.
Lu et al. "Combined PD-1 blockade and GITR triggering induce a potent antitumor immunity in murine cancer models and synergizes with chemotherapeutic drugs." Journal of translational medicine 12.1 (2014): 36.
Ma et al. "Paclitaxel Nano-Delivery Systems: A Comprehensive Review. J Nanomed Nanotechnol," 2013;4(2):1000164.
Mallow, et al, Broncho-Adventitial Delivery of Paclitaxel to Extend Airway Patency in Malignant airway Obstruction (broadway trial), Advances in Thoracic Oncologic Diagnostics, Abstract May 2017.
Marabelle, et al. "Starting the Fight in the Tumor: expert Recommendation for the Development of Human Intratumoral Immunotherapy (HIT-IT)" Published by Oxford University Press on behalf of the European Society for Medical Oncology. 2018.
Maude et al. "Chimeric Antigen Receptor T Cells for Sustained Remissions in Leukemia," N Engl J Med 371;16 Oct. 16, 2014.
Mayo Clinic—Patient care and health information regarding cycstic fibrosis, accessed online Sep. 10, 2018, pp. 1-8.

(56) References Cited

OTHER PUBLICATIONS

McKiernan et al, "Phase I trail of intravesical docetaxel in the management of superficial bladder cancer refractory to standard intravesical therapy" Journal of Clinical Oncology, vol. 24, No. 19, 2006.
McKiernan et. al. "Phase II Trial of intravesical nanoparticle albumin bound paclitaxel for the treatment of nonmuscle invasive urothelial carcinoma of the bladder after bacillus Calmette-guerin treatment failure" The Jounral of Urology, vol. 192, 1633-1638, 2014.
Merisko-Liversidge et al. "Nanosizing: a formulation approach for poorly-water-soluble compounds," European Journal of Pharmaceutical Sciences 18 (2003) 113-120.
Merisko-Liversidge, et al., "Formulation and Antitumor Activity Evaluation of Nanocrystalline Suspensions of Poorly Soluble Anticancer Drugs," Pharmaceutical Research, 13(2): 272-278, 1996.
Michels et. al. "Paclitaxel promotes differentiation of myeloid-derived suppressor cells into dendritic cells in vitro in a TLR4-independent manner". J Immunotoxicol. 2012; 9:292-300.
Miele et al. "Albumin-bound formulation of paclitaxel (Abraxane® ABI-007) in the treatment of breast cancer," International Journal of Nanomedicine 2009:4 99-105.
Mirvish et al. "Dendritic Cell Vaccines in Cancer: Obstacles to Overcome," Chapter 21, Dendritic Cells in Cancer, Shurin et al. (eds.) Springer Science+Business Media, LLC 2009.
Morales et al. "Growth-inhibiting effects on intralesional docetaxel and paclitaxel on an experimental model of malignant neuroectodermal tumor," Journal of Neuro-Oncology 59: 207-212, 2002.
Muller et al. "Challenges and solutions for the delivery of biotech drugs—a review of drug nanocrystal technology and lipid nanoparticles," Journal of Biotechnology 113 (2004) 151-170.
Narang et al. "Pharmaceutical Development and Regulatory Considerations for Nanoparticles and Nanoparticulate Drug Delivery Systems," Journal of Pharmaceutical Sciences 2013.
Nars et. al. "Immunomodulatory effects of low dose chemotherapy and perspectives of its combination with immunotherapy." International journal of cancer 132.11 (2013): 2471-2478.
Necchi et al., "918TiP: Pembrolizumab and nanoparticle albumin bound paclitaxel (nabpaclitaxel) for metastatic urothelial carcinoma (UC) after chemotherapy failure: the open-label, single-arm. phase 2 PEANUT study." Annals of Oncology 42nd ESMO Congress, ESMO 2017 Madrid Spain, 28(Supplement5):v325-v326 (Sep. 2017).
Nsereko et al. "Localized delivery of paclitaxel in solid tumors from biodegradable chitin microparticle formulations," Biomaterials 23 (2002) 2723-2731.
Nayyar et al. "Overcoming Resistance to Natural Keller Cell Based Immunotherapies for Solid Tumors," Frontiers in Oncology, vol. 9, Article 51, Feb. 11, 2019.
O'Shaughnessy, et al. "Systemic Antitumor Immunity by PD-1/PD-L1 Inhibition is Potentiated by Vascular-Targeted Photodynamic Therapy of Primary Tumors," Clinical Cancer Research, 24(3): 592-599, Sep. 2017.
Pankaj, et al., Nanosized Paclitaxel Particles from Supercritical Carbon Dioxide Processing and Their Biological Evaluation, LANGMUIR, 23(5): 2674-2679, Feb. 2007. (PATHAK ????).
Pettitt et al. "CAR-T Cells: A Systematic Review and Mixed Methods Analysis of the Clinical Trial Landscape," Molecular Therapy, vol. 26, No. 2, Feb. 2018.
Podczeck, "The Influence of Particle Size Distribution and Surface Roughness of Carrier Particles on the in vitro Properties of Dry Powder Inhalations," Aerosol Science and Technology, 31(4): 301-321, 1999.
Polo, et al, "Maintenance strategies in stage IV non-small-cell lung cancer (NSCLC): in which patients, with which drugs?" Annals of Oncology 25: 1283-1293, Dec. 2013.
Pretto et al. "Preclinical evaluation of IL2-based immunocytokines supports their use in combination with dacarbazine, paclitaxel and TNF-based immunotherapy." Cancer Immunology, Immunotherapy 63.9 (2014): 901-910.
PROVENGE® Presribing Information, Rev. Jul. 2017, 2 pages.
Raju et. al. "Review of checkpoint immunotherapy for the management of non-small cell lung cancer" Immuno Targets and Therapy, 2018;7 63-75.
Rampersaud et. al. "Commentary on Hyperthermia as a treatment for bladder cancer" Oncology 2010 24(12); 1155-1160.
De Smet et al., "Development of a Nanocrystalline Paclitaxel Formulation for Hipec Treatment" Pharm. Research 29:2398-2406 (2012).
FDA—"ABRAXANE—Prescribing Information" Oct. 1, 2012, pp. 1-19.
Gradishar, "Taxanes for the Treatment of Metastatic Breast Cancer" Breast Cancer: Basic and Clinical Research 6(1):159-71 (Jan. 2012).
Machiels et al., "Cyclophosphamide, Doxorubicin, and Paclitaxel Enhance the Antitumor Immune Response of Granulocyte/Macrophage-Colony Stimulating Factor-secreting Whole-Cell Vaccines in HER-2/neu Tolerized Mice" Cancer Research 61:3689-97 (May 2001).
Manthey et al., "Taxol increases steady-state levels of lipopolysaccharide-inducible genes and protein-tyrosine phosphorylation in murine macrophages" The Journal of Immunology 149(7):2459-2465 (Oct. 1992).
Monette et al., "Chitosan thermogels for local expansion and delivery of tumor-specific T lymphocytes towards enhanced cancer immunotherapies" Biomaterials 75:237-49 (Jan. 2016).
Zhong et al., "Low-dose paclitaxel prior to intratumoral dendtritic cell vaccine modulates intratumoral cytokine network and lung cancer growth" Clinical Cancer Research 13(18):5455-62 (Sep. 2007).
The International Search Report (ISR) with Written Opinion for PCT/US2018/036587 dated Sep. 13, 2018, pp. 1-17.
Kirtane, Tejas et al. "EUS for pancreatic cystic neoplasms: The roadmap to the future is much more than just a few shades of gray" Asian Pacific Journal of Tropical Medicine (2016) vol. 9(12), pp. 1218-1221.
U.S. Appl. No. 16/383,023, filed Jan. 4, 2019, Crititech, Inc.
U.S. Appl. No. 16/239,531, filed Jan. 4, 2019, Crititech, Inc.
U.S. Appl. No. 16/239,530, filed Jan. 4, 2019, Crititech, Inc.
U.S. Appl. No. 16/239,533, filed Jan. 4, 2019, Crititech, Inc.
U.S. Appl. No. 16/239,527, filed Jan. 4, 2019, Crititech, Inc.
U.S. Appl. No. 16/239,529, filed Jan. 4, 2019, Crititech, Inc.
U.S. Appl. No. 15/895,197, filed Feb. 13, 2018, Crititech, Inc.
U.S. Appl. No. 15/499,397, filed Apr. 27, 2017, Crititech, Inc.
U.S. Appl. No. 15/261,108, filed Sep. 9, 2016, Crititech, Inc.
U.S. Appl. No. 15/174,505, filed Jun. 6, 2016, Crititech, Inc.
U.S. Appl. No. 16/136,502, filed Sep. 20, 2018, Crititech, Inc.
U.S. Appl. No. 16/512,044, filed Jul. 15, 2019, Crititech, Inc.
U.S. Appl. No. 16/007,095, filed Jun. 13, 2018, Crititech, Inc.
U.S. Appl. No. 16/444,299, filed Jun. 18, 2019, Crititech, Inc.
U.S. Appl. No. 17/023,098, filed Sep. 16, 2020, Crititech, Inc.
U.S. Appl. No. 17/023,635, filed Sep. 17, 2020, Crititech, Inc.
clinicaltrials.gov "OGX-011 and Docetaxel in Treating Patients with Metastatic or Locally Recurrent Solid Tumors" May 10, 2007.
Goel, et al., "Exploring targeted pulmonary delivery for treatment of lung cancer," IntJ Pharm Investig (2013) 3(1):8-14.
Lu Shengjie et al: "Mucoadhesive polyacrylamide nanogel as a potential hydrophobic drug carrier for intravesical bladder cancer therapy", European Journal of Pharmaceutical Sciences, vol. 72, Mar. 2015, pp. 57-68.
NSST Technical Report, 1503-1, URL: https://www.nsst.nssmc.com/techrepo/zairyo_pdf/HRM-1503.pdf.
Rituraj Bharadwaj et al, "Topical delivery of paclitaxel for treatment of skin cancer," Drug Development and Industrial Pharmacy,vol. 42, No. 9, Mar. 2016, pp. 1482-1494.
Shikanov A et al: "Paclitaxel tumor biodistribution and efficacy after intratumoral injection of a biodegradable extended release implant", International Journal of Pharmaceutics, vol. 358, No. 1-2, Jun. 2008, pp. 114-120.
Shikanov et al. "Intratumoral Delivery of Paclitaxel for Treatment of Orthotopic Prostate Cancer," Journal of Pharmaceutical Sciences, vol. 98, No. 3, Mar. 2009.
Ze Lu et al, "Paclitaxel Gelatin Nanoparticles for Intravesical Bladder Cancer Therapy," Journal of Urology, vol. 185, No. 4, Apr. 2011, pp. 1478-1483.

(56) References Cited

OTHER PUBLICATIONS

Nadezhda V Koshkina et al: "Paclitaxel Liposome Aerosol Treatment Induces Inhibition of Pulmonary Metastases in Murine Renal Carcinoma Model", Clinical Cancer Research, Oct. 2001, pp. 3258-3262.

Le Visage, et al.,"Efficacy of PaclitaxelReleased From Bio-Adhesive Polymer Microspheres on Model Superficial Bladder Cancer," Journal of Urol, vol. 171, No. 3, Mar. 2004, pp. 1324-1329.

Al-Ghananeem et al. "Intratumoral Delivery of Paclitaxel in Solid Tumor from Biodegradable Hyaluronan Nanoparticle Formulations," AAPS PharmSciTech, vol. 10, No. 2, Jun. 2009.

Pazdur, et al., (The toxoids: paclitaxel (Taxol) and docetaxel (Taxotere, Cancer treatment reviews, 19(4): 351-386 (1993).

TREATMENT OF EPITHELIAL CYSTS BY INTRACYSTIC INJECTION OF ANTINEOPLASTIC PARTICLES

CROSS REFERENCE

This application is a Continuation of U.S. patent application Ser. No. 16/382,446, filed Apr. 12, 2019, which is a Continuation of International Application No. PCT/US2018/036587, filed on Jun. 8, 2018, which claims priority to U.S. Provisional Application No. 62/517,711, filed Jun. 9, 2017, all of which are incorporated by reference herein in their entirety.

FIELD OF THE INVENTION

The present invention generally relates to treatment of epithelial cystic neoplasms (cysts).

BACKGROUND

A cystic neoplasm (cyst) is an abnormal sac in the body that may be filled with a liquid or semisolid substance. A cyst can form in any part of the body, including bones, organs and soft tissues. Generally, cysts are noncancerous (benign), however, a benign cyst can be precancerous and change into a malignant growth. Epithelial cysts are cysts which have an inner epithelial lining. Examples of epithelial cysts include gastrointestinal cysts such as hepatic cysts, pancreatic cysts, splenic cysts, colon cysts; urologic cysts such as renal cysts, epididymal cysts, prostatic cysts; gynecological cysts such as ovarian cysts and vaginal cysts; head and neck cysts such as thyroid cysts, parathyroid cysts, and other head and neck cysts; as well as other cysts such as Baker's cysts, lung cysts, lymphatic cysts, and pericardial cysts.

Pancreatic cystic neoplasms are being detected with increasing frequency due to improved cross-sectional imaging and routine examination (Pitman 2010). Mucinous pancreatic cystic neoplasms represent approximately 75% of all pancreatic cystic neoplasms and are divided into two categories: intraductal papillary mucinous neoplasms (IPMNs) and mucinous cystic neoplasms (MCNs). Both types of mucinous pancreatic neoplasms may present with symptoms such as abdominal pair, pancreatitis, jaundice, weight loss, malabsorption, nausea, vomiting, and palpable abdominal mass (Tanaka 2005; Muthusamy 2016). Oftentimes, the cysts do not present any symptoms at all and are detected by chance because of the improved imaging when patients are being examined for other reasons.

Mucinous pancreatic cystic neoplasms have malignant potential, thus each patient diagnosed is at risk for developing pancreatic cancer (Farrell 2015; Sarr 2000). In a study of 401 patients with pancreatic cysts, 11% of resected cysts contained invasive cancer (Ferrone 2009). Patients diagnosed with IPMN have a 40% chance of invasive cancer and 58% have underlying malignant features, while those with MCN have a malignancy risk that varies between 10% and 50% (Greer 2016; Allen 2007). To avoid progression to pancreatic cancer, an aggressive and rapidly fatal disease, all patients with mucinous pancreatic cysts should be carefully evaluated and offered treatment (National Cancer Institute 2016, Fernández-del Castillo 1995).

An emerging treatment for mucinous pancreatic cysts is cyst fluid aspiration by endoscopic ultrasound-guided fine needle aspiration (EUS-FNA) followed by endoscopic ultrasound-guided (EUS-guided) ethanol lavage as an ablative agent in order to induce cell death by membrane lysis, protein denaturation, and vascular occlusion (Jani 2011; DeWitt 2009). However, studies examining cyst volume response to ethanol injection failed to standardize their techniques and ethanol concentration/volume, and a ten-year study conducted by Gómez 2016 demonstrated that only 9% of patients experienced complete cyst resolution (Gomez 2016; Kirtane 2016). There has been some controversy regarding the current treatment methods and practices for pancreatic cysts (Farrell 2013, Tanaka 2016, McGrath 2017).

Current methods for determining malignancy within mucinous cysts provide unreliable results. It is difficult to identify cyst histology without resection. Approximately 25% of non-operative histologic diagnoses are inaccurate. Physicians compensate for this deficit by recommending that patients with cysts with features such as symptoms, positive cytology, mural nodules, or greater than 3 cm undergo surgical resection (Pitman 2010). Due to the concerns of mucin leakage, pancreatic fistulae, and recurrence, the standard surgical treatment for invasive and non-invasive MCNs and IPMNs is pancreatectomy with lymph node dissection, rather than focal non-anatomic resections or resections without lymphadenectomy or splenectomy (Tanaka 2012). In a study of 37 high-volume centers (2694 patients), the pancreatectomy mortality rate was reported to be 1.3%, increasing to 3.0% in patients 80 years of age and over, with overall complication rates ranging from 20.0% to 72.2% (Tamirisa 2016). In patients that can be diagnosed with a malignancy rate of less than 3%, the risk of death from pancreatectomy is higher than that of malignancy (Allen 2007). Even after surgery, the recurrence rates of cysts can be as high as 20% (Tanaka 2012). Untreated cysts, however, may progress to malignant disease while under observation (Allen 2007).

SUMMARY OF THE INVENTION

The present invention provides solutions to the aforementioned limitations and deficiencies in the art relating to treatment of cystic neoplasms (cysts), particularly to treatment of epithelial cysts including pancreatic cysts, by injection of antineoplastic particles, such as taxane particles, directly into the cysts (intracystic injection). When a composition of antineoplastic particles, such as taxane particles (e.g., paclitaxel particles or docetaxel particles), are injected into a cyst, the antineoplastic particles will persist in the cyst for a longer time than a solution of antineoplastic agent injected into the cyst because solutions are more easily and quickly cleared from the cysts by the body. Although not bound by theory, it is hypothesized that the use of antineoplastic particles result in increased efficacy and decreased toxicity as compared with solutions of antineoplastic agents, at least in part, due to the slow release of the antineoplastic agent from the suspended particle. It also is hypothesized that because of the physical characteristics of the antineoplastic particles, they can embed within or on the inner epithelial lining of the cyst resulting in a longer residence time than with solutions or with albumin coated particles. Instillation of a suspension of antineoplastic particles directly into the pancreatic cyst creates a depot effect where the antineoplastic agent is slowly released from the particles into tire cyst, resulting in prolonged local exposure of the antineoplastic agent. Clearance from the pancreas is reduced, with lower systemic levels of antineoplastic agent, further limiting systemic toxicity. In a preferred embodiment, the antineoplastic particles are taxane particles such as paclitaxel particles or docetaxel particles.

In one aspect of the invention, disclosed are methods for treating epithelial cysts, the methods comprise injecting a composition comprising an effective amount of antineoplastic particles directly into the cyst (intracystic injection) thereby treating the epithelial cyst, wherein the particles have a mean particles size (number) of from 0.1 microns to 5 microns. In preferred embodiments, the antineoplastic particles are taxane particles. In some embodiments, the particles of the antineoplastic agent have a mean particle size (number) of from 0.1 microns to 1.5 microns. In some embodiments, the taxane particles are paclitaxel particles. In some embodiments, the composition and taxane particles exclude albumin. In other embodiments, the taxane particles are docetaxel particles. In some embodiments, the epithelial cyst is a pancreatic cyst such as a mucinous pancreatic cyst. In some embodiments, the epithelial cyst is reduced in volume/size, has reduced growth rate, is eliminated, or is ablated alter treatment by injection of the composition. In some embodiments, the pain associated with an epithelial cyst is reduced after injection of the composition.

In another aspect of the invention, disclosed are kits comprising: (a) a first vial comprising taxane particles; (b) a second vial comprising a pharmaceutically acceptable aqueous carrier and a surfactant; and (c) instructions for reconstituting the antineoplastic particles into a suspension useful for intracystic injection by: combining the contents of the first vial and the second vial to form the suspension and optionally diluting the suspension with a diluent. In some embodiments, the taxane particles have a mean particle size (number) of from 0.1 microns to 1.5 microns. In some embodiments, the surfactant is a polysorbate. In some embodiments, the taxane particles are paclitaxel particles. In other embodiments, the taxane particles are docetaxel particles.

Also, disclosed in the context of the present invention are the following embodiments 1 to 39:

Embodiment 1 is a method for treating an epithelial cyst, the method comprising injecting a composition comprising an effective amount of antineoplastic particles directly into the cyst, thereby treating the epithelial cyst, wherein the particles have a mean particle size (number) of from 0.1 microns to 5 microns.

Embodiment 2 is the method of embodiment 1, wherein the composition further comprises a liquid carrier, and wherein the composition comprises a suspension of the antineoplastic particles dispersed in the carrier.

Embodiment 3 is the method of embodiment 2, wherein the carrier is an aqueous carrier.

Embodiment 4 is the method of embodiment 3, wherein the aqueous carrier comprises 0.9% saline solution.

Embodiment 5 is the method of any one of embodiments 3 or 4, wherein the aqueous carrier comprises a surfactant.

Embodiment 6 is the method of embodiment 5, wherein the surfactant is a polysorbate.

Embodiment 7 is the method of embodiment 6, wherein the polysorbate is polysorbate 80, and wherein the polysorbate 80 is present in the aqueous carrier at a concentration of between about 0.01% v/v and about 1% v/v.

Embodiment 8 is the method of any one of embodiments 3 to 7, wherein the composition further comprises a diluent, wherein the carrier and the diluent form a mixture, and wherein the composition is a suspension of the antineoplastic particles dispersed in the carrier/diluent mixture.

Embodiment 9 is the method of embodiment 8, wherein the diluent is a 0.9% saline solution.

Embodiment 10 is the method of any one of embodiment 1 to 9, wherein the antineoplastic particles are taxane particles.

Embodiment 11 is the method of embodiment 10, wherein the taxane particles comprise at least 95% of the taxane, wherein the taxane particles have a mean particle size (number) of from 0.1 microns to 1.5 microns, and wherein the composition and taxane particles exclude albumin.

Embodiment 12 is the method of any one of embodiments 10 to 11, wherein the concentration of taxane particles in the composition is between about 6 mg/mL and about 15 mg/mL.

Embodiment 13 is the method of any one of embodiments 10 to 12, wherein the taxane particles are paclitaxel particles.

Embodiment 14 is the method of embodiment 13, wherein the paclitaxel particles have a specific surface area (SSA) of at least 18 $m^2/g$, 20 $m^2/g$, 25 $m^2/g$, 30 $m^2/g$, 32 $m^2/g$, 34 $m^2/g$, or 35 $m^2/g$; or from about 18 $m^2/g$ to about 50 $m^2/g$.

Embodiment 15 is the method of any one of embodiments 13 to 14, wherein the paclitaxel particles have a bulk density (not-tapped) of 0.05 $g/cm^3$ to 0.15 $g/cm^3$.

Embodiment 16 is the method of any one of embodiments 10 to 12, wherein the taxane particles are docetaxel particles.

Embodiment 17 is the method of embodiment 16, wherein the docetaxel particles have a specific surface area (SSA) of at least 18 $m^2/g$, 20 $m^2/g$, 25 $m^2/g$, 30 $m^2/g$, 35 $m^2/g$, 40 $m^2/g$, or 42 $m^2/g$; or from about 18 $m^2/g$ and about 60 $m^2/g$.

Embodiment 18 is the method of any one of embodiments 16 to 17, wherein the docetaxel particles have a bulk density (not-tapped) of 0.05 $g/cm^3$ to 0.15 $g/cm^3$.

Embodiment 19 is the method of any one of embodiments 1 to 18, wherein the cyst fluid is withdrawn from the cyst prior to injecting the composition.

Embodiment 20 is the method of embodiment 19, wherein the volume of the composition injected into the cyst is equal to the volume of cyst fluid removed from the cyst.

Embodiment 21 is the method of any one of embodiments 1 to 20, wherein the epithelial cyst is a pancreatic cyst.

Embodiment 22 is the method of embodiment 21, wherein the pancreatic cyst is a mucinous pancreatic cyst.

Embodiment 23 is the method of any one of embodiments 1 to 22, wherein the injection of the composition is conducted by endoscopic ultrasound-guided line needle injection (EUS-FNI).

Embodiment 24 is the method of any one of embodiments 1 to 25, wherein the epithelial cyst is reduced in volume/size, has reduced growth rate, is eliminated, or is ablated after injection of the composition, and/or wherein the pain associated with the cyst is reduced.

Embodiment 25 is the method of any one of embodiments 1 to 24, wherein the epithelial cyst is benign.

Embodiment 26 is a kit comprising:
  (a) a first vial comprising taxane particles;
  (b) a second vial comprising a pharmaceutically acceptable aqueous carrier and a surfactant; and
  (c) instructions for reconstituting the taxane particles into a suspension useful for intracystic injection by: combining the contents of the first vial and the second vial to form the suspension and optionally diluting the suspension with a diluent.

Embodiment 27 is the kit of embodiment 26, wherein the aqueous carrier is 0.9% saline solution, wherein the surfactant is a polysorbate, and wherein the polysorbate is at a concentration of between about 0.01% v/v and about 1% v/v.

Embodiment 28 is the kit of any one of embodiments 26 to 27, wherein the diluent is 0.9% saline solution.

Embodiment 29 is the kit of any one of embodiments 26 to 28, wherein the taxane particles comprise at least 95% of the taxane, wherein the taxane particles have a mean particle size (number) of from 0.1 microns to 1.5 microns, and wherein the taxane particles exclude albumin.

Embodiment 30 is the kit of any one of embodiments 26 to 29, wherein the taxane particles are solid, uncoated (neat) individual particles; wherein the taxane particles are not bound to any substance; wherein no substances are absorbed or adsorbed onto the surface of the taxane particles; wherein the taxane particles are not encapsulated, contained, enclosed or embedded within any substance; wherein the taxane particles are not coated with any substance; wherein the taxane particles are not microemulsions, nanoemulsions, microspheres, or liposomes; wherein the taxane particles are not bound to, encapsulated in, or coated with a monomer, a polymer (or biocompatible polymer), a protein a surfactant, or albumin; and/or wherein a monomer, a polymer (or biocompatible polymer), a protein, a surfactant, or albumin is not absorbed or adsorbed onto the surface of the taxane particles.

Embodiment 31 is the kit of any one of embodiments 26 to 30, wherein the taxane particles are paclitaxel particles.

Embodiment 32 is the kit of embodiment 31, wherein the paclitaxel particles have a specific surface area (SSA) of at least 18 $m^2/g$, 20 $m^2/g$, 25 $m^2/g$, 30 $m^2/g$, 32 $m^2/g$, 34 $m^2/g$, or 35 $m^2/g$; or from about 18 $m^2/g$ to about 50 $m^2/g$.

Embodiment 33 is the kit of any one of embodiments 31 to 32, wherein the paclitaxel particles have a bulk density (not-tapped) of 0.05 $g/cm^3$ to 0.15 $g/cm^3$.

Embodiment 34 is the kit of any one of embodiments 26 to 30, wherein the taxane particles are docetaxel particles.

Embodiment 35 is the kit of embodiment 34, wherein the docetaxel particles have a specific surface area (SSA) of at least 18 $m^2/g$, 20 $m^2/g$, 25 $m^2/g$, 30 $m^2/g$, 35 $m^2/g$, 40 $m^2/g$, or 42 $m^2/g$; or from about 18 $m^2/g$ and about 60 $m^2/g$.

Embodiment 36 is the kit of any one of embodiments 34 to 35, wherein the docetaxel particles have a bulk density (not-tapped) of 0.05 $g/cm^3$ to 0.15 $g/cm^3$.

Embodiment 37 is a method of administering a composition comprising antineoplastic particles to an epithelial cyst of a subject, the method comprising injecting the composition into the cyst using endoscopic ultrasound guided-fine needle injection, wherein the antineoplastic particles have a mean particle size (number) of from 0.1 microns to 5 microns, and wherein the antineoplastic particles are crystalline particles.

Embodiment 38 is the method of embodiment 37, wherein the antineoplastic particles have a mean particle size (number) of from 0.3 microns to 5 microns.

Embodiment 39 is the method of any one of embodiments 37 to 38, wherein the antineoplastic particles are taxane particles.

The term "antineoplastic agents" as used herein are drugs used to treat neoplasms including non-cancerous neoplasms and malignant neoplasms, and include "chemotherapeutic agents", which are drugs used to treat cancer. In a preferred embodiment, the antineoplastic agent is a taxane.

The terms "antineoplastic agent particles", "antineoplastic particles" or "particles of an antineoplastic agent", as used herein are particles of an antineoplastic agent and have a mean particle size (number) of from about 0.1 microns to about 5 microns (about 100 nm to about 5000 nm) in diameter. In a preferred embodiment, the antineoplastic particles are taxane particles.

As used herein, the terms "cystic neoplasm" and "cyst" can be used interchangeably and mean an abnormal sac in the body that may be filled with a liquid or semisolid substance. An "epithelial" cystic neoplasm or "epithelial" cyst, has an epithelial inner lining. In some embodiments, the epithelial cyst is benign. In some embodiments, the cyst is precancerous.

As used herein, the terms "treat", "treatment", "treated", or "treating" with respect to cystic neoplasms (cysts) means accomplishing one or more of the following: (a) reducing cyst volume/size; (h) reducing cyst growth rate; (c) eliminating a cyst; (d) ablation of a cyst; or (e) reducing pain associated with the cyst.

As used herein, the term "suspension" means a suspension dosage form composition where antineoplastic particles are dispersed (suspended) within a continuous earner or a continuous carrier/diluent mixture. The antineoplastic particles can be completely dispersed, partially dispersed and partially dissolved, but not completely dissolved in the carrier or carrier, diluent mixture.

The terms "subject" or "patient" as used herein mean a vertebrate animal. In some embodiments, the vertebrate animal can be a mammal. In some embodiments, the mammal can be a primate, including a human.

The term "room temperature" (RT) as used herein, means 20-25° C.

The term "surfactant" or "surface active agent" as used herein, means a compound or a material or a substance that exhibits the ability to lower the surface tension of water or to reduce the interfacial tension between two immiscible substances.

As used herein, the singular forms "a", "an" and "the" include plural referents unless the context clearly dictates otherwise. "And" as used herein is interchangeably used with "or" unless expressly stated otherwise.

The terms "about" or "approximately" as used herein mean +/− five percent (5%) of the recited unit of measure.

For this application, a number value with one or more decimal places can be rounded to the nearest whole number using standard rounding guidelines, i.e. round up if the number being rounded is 5,6,7,8, or 9; and round down if the number being rounded is 0, 1, 2, 3, or 4. For example, 3.7 can be rounded to 4.

Unless the context clearly requires otherwise, throughout the description and the claims, the words "comprise", "comprising", and the like are to be construed in an inclusive or open-ended sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application. The compositions and methods for their use can "comprise," "consist essentially of," or "consist of" any of the ingredients or steps disclosed throughout the specification. With respect to the phrase "consisting essentially of," a basic and novel property of the methods of the present invention are their ability to treat epithelial cystic neoplasms by intracystic injection of compositions of antineoplastic particles.

It is contemplated that any embodiment discussed in this specification can be implemented with respect to any method or composition of the invention, and vice versa.

furthermore, compositions of the invention cat be used to achieve methods of the invention.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

DETAILED DESCRIPTION OF THE INVENTION

Figure 1:
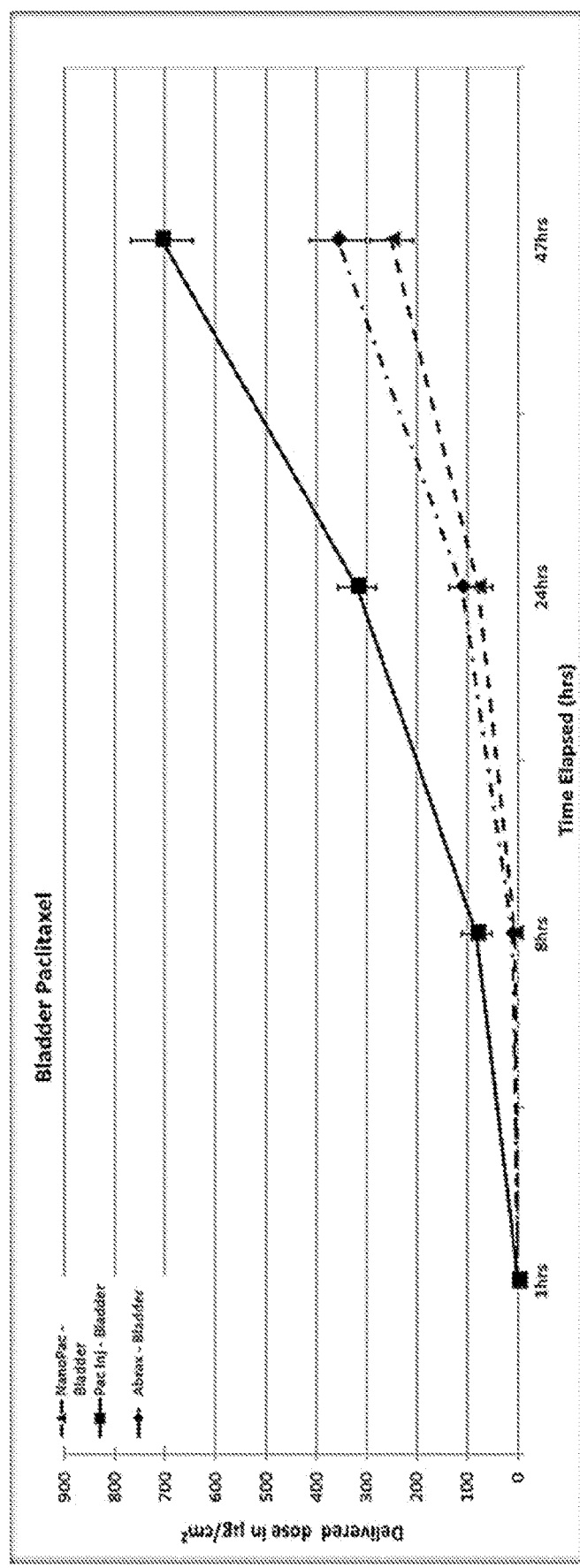
FIG. 1 is a graph of the flux of paclitaxel (delivered dose of paclitaxel active drug across a porcine bladder membrane over time) from various paclitaxel formulations.

In one aspect of the invention, disclosed are methods for treating epithelial cysts, the methods comprise injecting a composition comprising an effective amount of antineoplastic particles directly into the cyst (intracystic injection), thereby treating the cyst. In some embodiments, the composition further comprises a carrier, which can be an aqueous liquid carrier. In some embodiments, the carrier comprises a surfactant which can be a polysorbate, such as polysorbate 80. In other embodiments, the composition further comprises a carrier and a diluent, wherein the earner and diluent form a mixture. In some embodiments, the composition is a suspension wherein the antineoplastic particles are suspended in the carrier or the carrier/diluent mixture. In preferred embodiments, the antineoplastic particles are taxane particles. In some embodiments, the particles of the antineoplastic agent have a mean particle size (number) of from 0.1 microns to 1.5 microns. In some embodiments, the taxane particles are paclitaxel particles. In other embodiments, the taxane particles are docetaxel particles. In various embodiments, the methods further comprise withdrawal of the cyst fluid from the cyst prior to injecting the composition and injecting a volume of the composition equal to the volume of the withdrawn cyst fluid. In some embodiments, the epithelial cyst is a pancreatic cyst such as a mucinous pancreatic cyst. In some embodiments, the injection of the composition is conducted by endoscopic ultrasound-guided fine needle injection (EUS-FNI). In some embodiments, the epithelial cyst is reduced in volume/size, has reduced growth rate, is eliminated, or is ablated after treatment by injection of the composition. In some embodiments, the pain associated with the epithelial cyst is reduced.

In another aspect of the invention, disclosed are kits comprising: (a) a first vial comprising taxane particles; (b) a second vial comprising a pharmaceutically acceptable aqueous carrier and a polysorbate; and (c) instructions for reconstituting the antineoplastic particles into a suspension useful for intracystic injection by: combining the contents of the first vial and the second vial to form the suspension and optionally diluting the suspension with a diluent. In some embodiments, the taxane particles have a mean particle size (number) of from 0.1 microns to 1.5 microns. In some embodiments, the taxane particles are paclitaxel particles. In other embodiments, the taxane particles are docetaxel particles.

Antineoplastic Agent Particles

Antineoplastic agents are drugs used to treat neoplasms including malignant, pre-cancerous, and non-malignant neoplasms, and include "chemotherapeutic agents", which are drugs used to treat cancer. Non-limiting examples of antineoplastic agents include taxanes such as paclitaxel, derivatives of paclitaxel, docetaxel, cabazitaxel; epothilones; Vinca alkaloids such as vinblastine, vincristine, vindesine, vinorelbine; camptothecins such as topotecan; platinum complexes such as cisplatin, carboplatin, oxaliplatin; podophyllotoxins such as etoposide and teniposide; and 5-fluorouracil. Other non-limiting examples can be found listed in the "Ashgate Handbook of Antineoplastic Agents", published by Gower Publishing Limited, 2000, herein incorporated by reference. The antineoplastic agent particles have a mean particle size (number) of from about 0.1 microns to about 5 microns (about 100 nm to about 5000 nm) in diameter. In some embodiments, the antineoplastic agent particles have a mean particle size (number) of from about 0.1 microns to about 1.5 microns (about 100 nm to about 1500 nm) in diameter. In some embodiments, the antineoplastic agent particles have a mean particle size (number) of from about 0.1 microns to less than 1 micron (about 100 nm to less than 1000 nm) in diameter.

In preferred embodiments, the antineoplastic particles are solid, uncoated ("neat" or "naked") individual particles. In some embodiments, the antineoplastic particles are not bound to any substance. In some embodiments, no substances are absorbed or adsorbed onto the surface of the antineoplastic particles. In some embodiments, the antineoplastic agents or antineoplastic particles are not encapsulated, contained, enclosed or embedded within any substance. In some embodiments, the antineoplastic particles are not coated with any substance. In some embodiments, the antineoplastic particles are not microemulsions, nanoemulsions, microspheres, or liposomes containing an antineoplastic agent. In some embodiments, the antineoplastic particles are not bound to, encapsulated in, or coated with a monomer, a polymer (or biocompatible polymer), a protein, a surfactant, or albumin, in some embodiments, a monomer, a polymer tor biocompatible polymer), a protein, a surfactant, or albumin is not absorbed or adsorbed onto the surface of the antineoplastic particles. In some embodiments, the antineoplastic particles are in crystalline form. In other embodiments, the antineoplastic particles are is amorphous form, or a combination of both crystalline and amorphous form. In some embodiments, the antineoplastic particles of the invention contain traces of impurities and byproducts typically found during preparation of the antineoplastic agent. In some embodiments, the antineoplastic particles comprise at least 90%, at least 95%, at least 96%, at least 97%, at least 98%, at least 99% or 100% of the antineoplastic agent, meaning the antineoplastic particles consist of or consist essentially of substantially pure antineoplastic agent.

In a preferred embodiment, the ant neoplastic particles are taxane particles. Taxanes are poorly water soluble compounds generally having a solubility of less than or equal to 10 mg/mL in water at room temperature. Taxanes are widely used as antineoplastic agents and chemotherapy agents. The term "taxanes" as used herein include paclitaxel (I), docetaxel (II), cabazitaxel (III), and any other taxane or taxane derivatives, non-limiting examples of which are taxol B (cephalomannine), taxol C, taxol D, taxol E, taxol F, taxol G, taxadiene, baccatin III, 10-deacetylbaccatin, taxchinin A, brevifoliol, and taxuspine D, and also include pharmaceutically acceptable salts of taxanes.

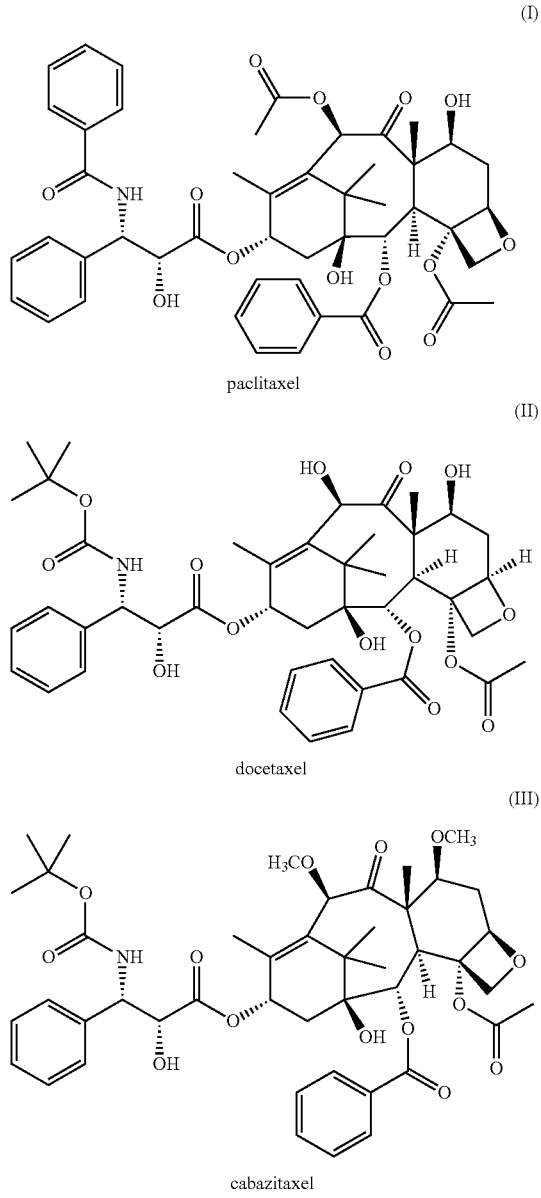

paclitaxel (I)

docetaxel (II)

cabazitaxel (III)

Paclitaxel and docetaxel active pharmaceutical ingredients (APIs) are commercially available from Phyton Biotech LLC, Vancouver, Canada. The docetaxel API contains not less than 90%, or not less than 95%, or not less than 97.5% docetaxel calculated on the anhydrous, solvent-free basis. The paclitaxel API contains not less titan 90%, or not less than 95%, or not less than 97% paclitaxel calculated on the anhydrous, solvent-free basis. In some embodiments, the paclitaxel API and docetaxel API are USP and/or BP grade. Paclitaxel API can be prepared from a semisynthetic chemical process or from a natural source such as plant cell fermentation or extraction. Paclitaxel is also sometimes referred to by the trade name TAXOL, although this is a misnomer because TAXOL is the trade name of a solution of paclitaxel in polyoxyethylated castor oil and ethanol intended for dilution with a suitable parenteral fluid prior to intravenous infusion. Taxane APIs can be used to make taxane particles. The taxane particles can be paclitaxel particles, docetaxel particles, or cabazitaxel particles, or particles of other taxane derivatives, including particles of pharmaceutically acceptable salts of taxanes.

Taxane particles have a mean particle size (number) of from about 0.1 microns to about 5 microns (about 100 nm to about 5000 nm) in diameter. In some embodiments, the taxane particles have a mean particle size (number) of from about 0.1 microns to about 1.5 microns (about 100 nm to about 1500 nm) in diameter. In some embodiments, the taxane particles have a mean particle size (number) of from about 0.1 microns to less than micron (about 100 nm to less than 1000 nm) in diameter. In preferred embodiments, the taxane particles are solid, uncoated (neat) individual particles. In some embodiments, the taxane particles are not bound to any substance. In some embodiments, no substances are absorbed or adsorbed onto the surface of the taxane particles. In some embodiments, the taxane or taxane particles are not encapsulated, contained, enclosed or embedded within any substance. In some embodiments, the taxane particles are not coated with any substance. In some embodiments, the taxane particles are not microemulsions, nanoemulsions, microspheres, or liposomes containing a taxane. In some embodiments, the taxane particles are not bound to, encapsulated in, or coated with a monomer, a polymer (or biocompatible polymer), a protein, a surfactant, or albumin. In some embodiments, a monomer, a polymer (or biocompatible polymer), a protein, a surfactant, or albumin is not absorbed or adsorbed onto the surface of the taxane particles. In some embodiments, the taxane particles exclude albumin. In some embodiments, the taxane particles are paclitaxel particles and exclude albumin. In some embodiments, the taxane particles are in crystalline form. In other embodiments, the taxane particles are in amorphous form, or a combination of both crystalline and amorphous form. In some embodiments, the taxane particles of the invention contain traces of impurities and byproducts typically found during preparation of the taxane. In some embodiments, the taxane particles comprise at least 90%, at least 95%, at least 96%, at least 97%, at least 98%, at least 99% or 100% of the taxane, meaning the taxane particles consist of or consist essentially of substantially pure taxane.

The antineoplastic particles or taxane particles (including paclitaxel particles, docetaxel particles, or cabazitaxel particles) can have a mean particle size (number) of from 0.1 microns to 5 microns, or from 0.1 microns to 2 microns, or from 0.1 microns to 1.5 microns, or from 0.1 microns to 1.2 microns, or from 0.1 microns to 1 micron, or from 0.1 microns to less than 1 micron, or from 0.1 microns to 0.9 microns, or from 0.1 microns to 0.8 microns, or from 0.1 to 0.7 microns, or from 0.2 microns to 5 microns, or from 0.2 microns to 2 microns, or from 0.2 microns to 1.5 microns, or from 0.2 microns to 1.2 microns, or from 0.2 microns to 1 micron, or from 0.2 microns to less than 1 micron, or from 0.2 microns to 0.9 microns, or from 0.2 microns to 0.8 microns, or from 0.2 microns to 0.7 microns, or from 0.3 microns to 5 microns, or from 0.3 microns to 2 microns, or from 0.3 microns to 1.5 microns, or from 0.3 microns to 1.2 microns, or from 0.3 microns to 1 micron, or from 0.3 microns to less than 1 micron, or from 0.3 microns to 0.9 microns, or from 0.3 microns to 0.8 microns, or from 0.3 microns to 0.7 microns, or from 0.4 microns to 5 microns, or from 0.4 microns to 2 microns, or from 0.4 microns to 1.5 microns, or from 0.4 microns to 1.2 microns, or from 0.4 microns to 1 micron, or from 0.4 microns to less than 1 micron, or from 0.4 microns to 0.9 microns, or from 0.4 microns to 0.8 microns, or from 0.4 microns to 0.7 microns, or from 0.5 microns to 5 microns, or from 0.5 microns to 2 microns, or from 0.5 microns to 1.5 microns, or from 0.5 microns to 1.2 microns, or from 0.5 microns to 1 micron, or from 0.5 microns to less than 1 micron, or from 0.5 microns to 0.9 microns, or from 0.5 microns to 0.8 microns, or from 0.5 microns to 0.7 microns, or from 0.6 microns to 5 microns, or from 0.6 microns to 2 microns, or from 0.6 microns to 1.5 microns, or from 0.6 microns to 1.2 microns, or from 0.6 microns to 1 micron, or from 0.6 microns to less than 1 micron, or from 0.6 microns to 0.9 microns, or from 0.6 microns to 0.8 microns, or from 0.6 microns to 0.7 microns.

The particle size of the antineoplastic particles including taxane particles can be determined by a particle size analyzer instrument and the measurement is expressed as the mean diameter based on a number distribution (number). A suitable particle size analyzer instrument is one which employs the analytical technique of light obscuration, also referred to as photozone or single particle optical sensing (SPOS). A suitable light obscuration particle size analyzer instrument is the ACCUSIZER, such as the ACCUSIZER 780 SIS, available from Particle Sizing Systems, Port Richey, Fla.. Another suitable particle size analyzer instrument is one which employs laser diffraction, such as the Shimadzu SALD-7101.

Antineoplastic agent particles including taxane particles can be manufactured using various particle size-reduction methods and equipment known in the art. Such methods include, but are not limited to conventional particle size-reduction methods such as wet or dry milling, micronizing, disintegrating, and pulverizing. Other methods include "precipitation with compressed anti-solvents" (PCA) such as with supercritical carbon dioxide. In various embodiments, the antineoplastic and/or taxane particles are made by PCA methods as disclosed in US patents U.S. Pat. Nos. 5,874,029, 5,833,591, 6,113,795, 7,744,923. 8,778,181, 9,233,348; US publications US 2015/0375153, US 2016/0354336, US 2016/0374953; and international patent application publications WO 2016/197091, WO 2016/197100, and WO 2016/197101; all of which are herein incorporated by reference.

In PCA particle size reduction methods using supercritical carbon dioxide, supercritical carbon dioxide (anti-solvent) and solvent, e.g. acetone or ethanol, are employed to generate uncoated antineoplastic or taxane particles as small as 0.1 to 5 microns within a well-characterized particle-size distribution. The carbon dioxide and solvent are removed during processing (up to 0.5% residual solvent may remain), leaving antineoplastic or taxane particles as a powder. Stability studies show that the paclitaxel particle powder is stable in a vial dose form when stored at room temperature for up to 59 months and under accelerated conditions (40° C./75% relative humidity) for up to six months.

Taxane particles produced by various supercritical carbon dioxide particle size reduction methods can have unique physical characteristics as compared to taxane particles produced by conventional particle size reduction methods using physical impacting or grinding, e.g., wet or dry milling, micronizing, disintegrating, comminuting, microfluidizing, or pulverizing. As disclosed in US publication 2016/0374953, herein incorporated by reference, such unique characteristics include a bulk density (not tapped) between 0.05 g/$cm^3$ and 0.15 g/$cm^3$ and a specific surface area (SSA) of at least 18 $m^2$/g of taxane (e.g., paclitaxel and docetaxel) particles, which are produced by the supercritical carbon dioxide particle size reduction methods described in US publication 2016/0374953 and as described below. This bulk density range is generally lower than the bulk density of taxane particles produced by conventional means, and the SSA is generally higher than the SSA of taxane particles produced by conventional means. These unique characteristics result in significant increases in dissolution rates in water/methanol media as compared to taxanes produced by conventional means. As used herein, the "specific surface area" (SSA) is the total surface area of the taxane particle per unit of taxane mass as measured by the Brunauer-Emmett-Teller ("BET") isotherm by the following method: a known mass between 200 and 300 mg of the analyte is added to a 30 mL sample tube. The loaded lube is then mounted to a Porous Materials Inc. SORPTOMETER®, model BET-202A. The automated test is then carried out using the BETWIN® software package and the surface area of each sample is subsequently calculated. As will be understood by those of skill in the art, the "taxane particles" can include both agglomerated taxane particles and non-agglomerated taxane particles; since the SSA is determined on a per gram basis it takes into account both agglomerated and non-agglomerated taxane particles in the composition. The BET specific surface area test procedure is a compendial method included in both the United States Pharmaceopeia and the European Pharmaceopeia. The bulk density measurement can be conducted by pouring the taxane particles into a graduated cylinder without tapping at room temperature, measuring the mass and volume, and calculating the bulk deadly.

As disclosed in US publication 2016/0374953, studies showed a SSA of 15.0 m2/g and a bulk density of 0.31 g/$cm^3$ for paclitaxel particles produced by milling paclitaxel in a Deco-PBM-V-0.41 ball mill suing a 5 mm ball size, at 600 RPM for 60 minutes at room temperature. Also disclosed in US publication 2016/0374953, one lot of paclitaxel particles had a SSA of 37.7 $m^2$/g and a bulk density of 0.085 g/$cm^3$ when produced by a supercritical carbon dioxide method using the following method: a solution of 65 mg/mL of paclitaxel was prepared in acetone. A BETE Micro Whirl® fog nozzle (BETE Fog Nozzle, Inc.) and a sonic probe (Qsonica, model number Q700) were positioned in the crystallization chamber approximately 8 mm apart. A stainless steel mesh filler with approximately 100 nm holes was attached to the crystallization chamber to collect the precipitated paclitaxel particles. The supercritical carbon dioxide was placed in the crystallization chamber of the manufacturing equipment and brought to approximately 1200 psi at about 38° C. and a flow rate of 24 kg/hour. The sonic probe was adjusted to 60% of total output power at a frequency of 20 kHz. The acetone solution containing the paclitaxel was pumped through the nozzle at a flow rate of 4.5 mL/minute for approximately 36 hours. Additional lots of paclitaxel particles produced by the supercritical carbon dioxide method described above had SSA values of: 22.27 $m^2$/g, 23.90 $m^2$/g, 26.19 $m^2$/g, 30.02 $m^2$/g, 31.16 $m^2$/g, 31.70 $m^2$/g, 32.59 $m^2$/g, 33.82 $m^2$/g, 35.90 $m^2$/g, 38.22 $m^2$/g, and 38.52 $m^2$/g.

As disclosed in US publication 2016/0374953, studies showed a SSA of 15.2 $m^2$/g and a bulk density of 0.44 g/$cm^3$ for docetaxel particles produced by milling docetaxel in a Deco-PBM-V-0.41 ball mill suing a 5 mm ball size, at 600 RPM for 60 minutes at room temperature. Also disclosed in US publication 2016/0374953, docetaxel particles had a SSA of 44.2 $m^2$/g and a bulk density of 0.079 g/$cm^3$ when produced by a supercritical carbon dioxide method using the following method: A solution of 79.32 mg/mL of docetaxel was prepared in ethanol. The nozzle and a sonic probe were positioned in the pressurizable chamber approximately 9 mm apart. A stainless steel mesh filter with approximately 100 nm holes was attached to the pressurizable chamber to collect the precipitated docetaxel particles. The supercritical carbon dioxide was placed in the pressurizable chamber of the manufacturing equipment and brought to approximately 1200 psi at about 38° C. and a flow rate of 68 slpm. The sonic probe was adjusted to 60% of total output power at a frequency of 20 kHz. The ethanol solution containing the docetaxel was pumped through the nozzle at a flow rate of 2 mL/minute for approximately 95 minutes). The precipitated docetaxel agglomerates and particles were then collected from the supercritical carbon dioxide as the mixture is pumped through the stainless steel mesh filter. The filter containing the particles of docetaxel was opened and the resulting product was collected from the filter.

As disclosed in US publication 2016/0374953, dissolution studies showed an increased dissolution rate in methanol/water media of paclitaxel and docetaxel particles made by the supercritical carbon dioxide methods described in US publication 2016/0374953 as compared to paclitaxel and docetaxel particles made by milling paclitaxel and docetaxel using a Deco-PBM-V-0.41 ball mill suing a 5 mm ball size, at 600 RPM for 60 minutes at room temperature. The procedures used to determine the dissolution rates are as follows. For paclitaxel, approximately 50 mg of material were coated on approximately 1.5 grams of 1 mm glass beads by tumbling the material and leads in a vial for approximately 1 hour. Beads were transferred to a stainless steel mesh container and placed in the dissolution bath containing methanol/water 50/50 (v/v) media at 37° C., pH 7, and a USP Apparatus II (Paddle), operating at 75 rpm. At 10, 20, 30, 60, and 90 minutes, a 5 mL aliquot was removed, filtered through a 0.22 μm filter and analyzed on a UV/VIS spectrophotometer at 227 nm. Absorbance values of the samples were compared to those of standard solutions prepared in dissolution media to determine the amount of material dissolved. For docetaxel, approximately 50 mg of material was placed directly in the dissolution bath containing methanol/water 15/85 (v/v) media at 37° C., pH 7, and a USP Apparatus II (Paddle), operating at 75 rpm. At 5, 15, 30, 60, 120 and 225 minutes, a 5 mL aliquot was removed, filtered through a 0.22 μm filter, and analyzed on a UV/VIS spectrophotometer at 232 nm. Absorbance values of the samples were compared to those of standard solutions prepared in dissolution media to determine the amount of material dissolved. For paclitaxel, the dissolution rate was 47% dissolved in 30 minutes for the particles made by the supercritical carbon dioxide method versus 32% dissolved it 30 minutes for the particles made by milling. For docetaxel, the dissolution rate was 27% dissolved in 30 minutes for the particles made by the supercritical carbon dioxide method versus 9% dissolved in 30 minutes for the particles made by milling.

In some embodiments, the antineoplastic particles have a SSA of at least 10, at least 12, at least 14, at least 16, at least 18, at least 19, at least 20, at least 21, at least 22, at least 23, at least 24, at least 25, at least 26, at least 27, at least 28, at least 29, at least 30, at least 31, at least 32, at least 33, at least 34, or at least 35 $m^2/g$. In one embodiment, the antineoplastic particles have an SSA of between about 10 $m^2/g$ and about 50 $m^2/g$. In some embodiments, the antineoplastic particles have a bulk density between about 0.050 $g/cm^3$ and about 0.20 $g/cm^3$.

In further embodiments, the antineoplastic particles have a SSA of:
(a) between 16 $m^2/g$ and 31 $m^2/g$ or between 32 $m^2/g$ and 40 $m^2/g$;
(b) between 16 $m^2/g$ and 30 $m^2/g$ or between 32 $m^2/g$ and 40 $m^2/g$;
(c) between 16 $m^2/g$ and 29 $m^2/g$ or between 32 $m^2/g$ and 40 $m^2/g$;
(d) between 17 $m^2/g$ and 31 $m^2/g$ or between 32 $m^2/g$ and 40 $m^2/g$;
(e) between 17 $m^2/g$ and 30 $m^2/g$ or between 32 $m^2/g$ and 40 $m^2/g$;
(f) between 17 $m^2/g$ and 29 $m^2/g$, or between 32 $m^2/g$ and 40 $m^2/g$;
(g) between 16 $m^2/g$ and 31 $m^2/g$ or between 33 $m^2/g$ and 40 $m^2/g$;
(h) between 16 $m^2/g$ and 30 $m^2/g$ or between 33 $m^2/g$ and 40 $m^2/g$;
(i) between 16 $m^2/g$ and 29 $m^2/g$ or between 33 $m^2/g$ and 40 $m^2/g$;
(j) between 17 $m^2/g$ and 31 $m^2/g$ or between 33 $m^2/g$ and 40 $m^2/g$;
(k) between 17 $m^2/g$ and 30 $m^2/g$ or between 33 $m^2/g$ and 40 $m^2/g$;
(l) between 17 $m^2/g$ and 29 $m^2/g$, or between 33 $m^2/g$ and 40 $m^2/g$;
(m) between 16 $m^2/g$ and 31 $m^2/g$, or ≥32 $m^2/g$;
(h) between 17 $m^2/g$ and 31 $m^2/g$, or ≥32 $m^2/g$:
(i) between 16 $m^2/g$ and 30 $m^2/g$, or ≥32 $m^2/g$;
(j) between 17 $m^2/g$ and 30 $m^2/g$, or ≥32 $m^2/g$;
(k) between 16 $m^2/g$ and 29 $m^2/g$, or ≥32 $m^2/g$;
(l) between 17 $m^2/g$ and 29 $m^2/g$, or ≥32 $m^2/g$;
(m) between 16 $m^2/g$ and 31 $m^2/g$, or ≥33 $m^2/g$;
(n) between 17 $m^2/g$ and 31 $m^2/g$, or ≥33 $m^2/g$;
(o) between 16 $m^2/g$ and 30 $m^2/g$, or ≥33 $m^2/g$;
(p) between 17 $m^2/g$ and 30 $m^2/g$, or ≥33 $m^2/g$;
(q) between 16 $m^2/g$ and 29 $m^2/g$, or ≥33 $m^2/g$; or
(r) between 17 $m^2/g$ and 29 $m^2/g$, or ≥33 $m^2/g$.

In some embodiments, the antineoplastic particles are taxane particles. In some embodiments, the antineoplastic particles or taxane particles are non-agglomerated individual particles and are not clusters of multiple antineoplastic or taxane particles.

In some embodiments, the taxane particles are paclitaxel particles and have an SSA of at least 18, at least 19, at least 20, at least 21, at least 22, at least 23, at least 24, at least 25, at least 26, at least 27, at least 28, at least 29, at least 30, at least 31, at least 32, at least 33, at least 34, or at least 35 $m^2/g$. In other embodiments, the paclitaxel particles have an SSA of 18 $m^2/g$ to 50 $m^2/g$, or 20 $m^2/g$ to 50 $m^2/g$, or 22 $m^2/g$ to 50 $m^2/g$, or 25 $m^2/g$ to 50 $m^2/g$, or 26 $m^2/g$ to 50 $m^2/g$, or 30 $m^2/g$ to 50 $m^2/g$, or 35 $m^2/g$ to 50 $m^2/g$, or 18 $m^2/g$ to 45 $m^2/g$, or 20 $m^2/g$ to 45 $m^2/g$, or 22 $m^2/g$ to 45 $m^2/g$, or 25 $m^2/g$ to 45 $m^2/g$, or 26 $m^2/g$ to 45 $m^2/g$, or 30 $m^2/g$ to 45 $m^2/g$, or 35 $m^2/g$ to 45 $m^2/g$, or 18 $m^2/g$ to 40 $m^2/g$, or 20 $m^2/g$ to 40 $m^2/g$, or 22 $m^2/g$ to 40 $m^2/g$, or 25 $m^2/g$ to 40 $m^2/g$, or 26 $m^2/g$ to 40 $m^2/g$, or 30 $m^2/g$ to 40 $m^2/g$, or 35 $m^2/g$ to 40 $m^2/g$.

In some embodiments, the paclitaxel particles have a bulk density (not-tapped) of 0.05 $g/cm^3$ to 0.15 $g/cm^3$, or 0.05 $g/cm^3$ to 0.20 $g/cm^3$.

In some embodiments, the paclitaxel particles have a dissolution rate of at least 40% w/w dissolved in 30 minutes or less in a solution of 50% methanol/50% water (v/v) in a USP II paddle apparatus operating at 75 RPM, at 37° C., and at a pH of 7.

In some embodiments, the taxane particles are docetaxel particles and have an SSA of at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, or at least 42 m$^2$/g. In other embodiments, the docetaxel particles have an SSA of 18 m$^2$/g to 60 m$^2$/g, or 22 m$^2$/g to 60 m$^2$/g, or 25 m$^2$/g to 60 m$^2$/g, or 30 m$^2$/g to 60 m$^2$/g, or 40 m$^2$/g to 60 m$^2$/g, or 18 m$^2$/g to 50 m$^2$/g, or 22 m$^2$/g to 50 m$^2$/g, or 25 m$^2$/g to 50 m$^2$/g, or 26 m$^2$/g to 50 m$^2$/g, or 30 m$^2$/g to 50 m$^2$/g, or 35 m$^2$/g to 50 m$^2$/g, or 40 m$^2$/g to 50 m$^2$/g.

In some embodiments, the docetaxel particles have a bulk density (not-tapped) of 0.05 g/cm$^3$ to 0.15 g/cm$^3$.

In some embodiments, the docetaxel particles have a dissolution rate of at least 20% w/w dissolved in 30 minutes or less in a solution of 15% methanol/85% water (v/v) in a USP II paddle apparatus operating at 75 RPM, at 37° C. and at a pH of 7.

The antineoplastic particles, including taxane particles, can be packaged into any suitable container such as glass or plastic vials. A non-limiting example of a suitable container is a Type 1, USP, clear-glass vial closed with a bromobutyl rubber stopper and aluminum crimp seal. The antineoplastic particles can be sterilized after the particles are in the container using sterilization methods known in the art such as gamma irradiation or autoclaving.

Compositions

The compositions of the invention comprise antineoplastic particles, such as taxane particles. The compositions can further comprise a carrier. The carrier can be a liquid (fluid) carrier, such as an aqueous carrier. Non-limiting examples of suitable aqueous carriers include water, such as Sterile Water for Injection USP; 0.9% saline solution (normal saline), such as 0.9% Sodium Chloride for Injection USP; dextrose solution, such as 5% Dextrose for Injection USP; and Lactated Ringer's Solution for Injection USP. Non-aqueous based liquid carriers and other aqueous-based liquid carriers can be used. The carrier can be a pharmaceutically acceptable carrier, i.e., suitable for administration to a subject by injection or other routes of administration. The carrier can be any other type of liquid such as emulsions or flowable semi-solids. Non-limiting examples of flowable semisolids include gels and thermosetting gels. The composition can be a suspension, i.e., a suspension dosage form composition where the antineoplastic particles, such as taxane particles, are dispersed (suspended) within a continuous carrier and/or diluent. The antineoplastic particles can be completely dispersed, partially dispersed and partially dissolved, but not completely dissolved in the carrier. In some embodiments, the composition is a suspension of taxane particles dispersed within a continuous carrier. In a preferred embodiment, the carrier is a pharmaceutically acceptable carrier. In preferred embodiments, the composition is sterile. In various embodiments, the composition comprises, consists essentially of, or consists of antineoplastic particles and a liquid carrier, wherein the composition is a suspension of the antineoplastic particles dispersed within the liquid carrier. In some embodiments, the composition consists essentially of or consists of antineoplastic particles and a carrier, wherein the carrier is an aqueous carrier and wherein the composition is a suspension.

The composition of antineoplastic particles and a carrier can be administered as-is. Optionally, the composition of antineoplastic particles and a carrier can further comprise a suitable diluent to dilute the composition in order to achieve a desired concentration (dose) of antineoplastic particles. In some embodiments, the carrier can serve as the diluent; stated another way, the amount of carrier in the composition provides the desired concentration of antineoplastic particles in the composition and no further dilution is needed. A suitable diluent can be a fluid, such as an aqueous fluid. Non-limiting examples of suitable aqueous diluents include water, such as Sterile Water for Injection USP; 0.9% saline solution (normal saline), such as 0.9% Sodium Chloride for Injection USP; dextrose solution, such as 5% Dextrose for Injection USP; and Lactated Ringer's Solution for Injection USP. Other liquid and aqueous-based diluents suitable for administration by injection can be used and can optionally include salts, buffering agents, and/or other excipients. In some embodiments, the diluent is sterile. The composition can be diluted with the diluent at a ratio to provide a desired concentration dosage of the antineoplastic particles. For example, the volume ratio of composition to diluent might be in the range of 1:1—1:100 v/v or other suitable ratios. In some embodiments, the composition comprises antineoplastic particles, a carrier, and a diluent, wherein the carrier and diluent form a mixture, and wherein the composition is a suspension of antineoplastic particles dispersed in the carrier/diluent mixture. In some embodiments, the carrier/diluent mixture is a continuous phase and the antineoplastic particles are a dispersed phase.

The composition, carrier, and/or diluent can further comprise functional ingredients such as buffers, salts, osmotic agents, surfactants, viscosity modifiers, rheology modifiers, suspending agents, pH adjusting agents such as alkalinizing agents or acidifying agents, tonicity adjusting agents, preservatives, antimicrobial agents including quaternary ammonium compounds such as benzalkonium chloride and benzethonium chloride, demulcents, antioxidants, anti foaming agents, alcohols such as ethanol, chelating agents, and/or colorants. For example, the composition can comprise taxane particles and a carrier comprising water, a salt, a surfactant, and optionally a buffer. In one embodiment, the carrier is an aqueous carrier and comprises a surfactant, wherein the concentration of the surfactant is 1% or less on a w/w or w/v basis; in other embodiments, line surfactant is less titan 0.5%, less than 0.25%, less than 0.1%, or about 0.1% In other embodiments, the aqueous carrier excludes the surfactants GELUCIRE® (polyethylene glycol glycerides composed of mono-, di- and triglycerides and mono- and diesters of polyethylene glycol) and or CREMOPHOR® (polyethoxylated castor oil). In some embodiments, the composition or carrier excludes polymers, proteins (such as albumin), polyethoxylated castor oil, and or polyethylene glycol glycerides composed of mono-, di- and triglycerides and mono- and diesters of polyethylene glycol.

The composition, carrier, and/or diluent can comprise one or more surfactants. Suitable surfactants include by way of example and without limitation polysorbates, lauryl sulfates, acetylated monoglycerides, diacetylated monoglycerides, and poloxamers, such as poloxamer 407. Polysorbates are polyoxyethylene sorbitan fatty acid esters which are a series of partial fatty acid esters of sorbitol and its anhydrides copolymerized with approximately 20, 5, or 4 moles of ethylene oxide for each mole of sorbitol and its anhydrides. Non-limiting examples of polysorbates are polysorbate 20, polysorbate 21, polysorbate 40, polysorbate 60, polysorbate 61, polysorbate 65, polysorbate 80, polysorbate 81, polysorbate 85, and polysorbate 120. Polysorbates containing approximately 20 moles of ethylene oxide are hydrophilic nonionic surfactants. Examples of polysorbates containing approximately 20 moles of ethylene oxide include polysorbate 20, polysorbate 40, polysorbate 60, polysorbate 65, polysorbate 80, polysorbate 85, and polysorbate 120. Polysorbates are available commercially from Croda under the tradename TWEEN™. The number designation of the polysorbate corresponds to the number designation of the TWEEN, e.g., polysorbate 20 is TWEEN 20, polysorbate 40 is TWEEN 40, polysorbate 60 is TWEEN 60, polysorbate 80 is TWEEN 80, etc. USP/NF grades of polysorbate include polysorbate 20 NF, polysorbate 40 NF, polysorbate 60 NF, and polysorbate 80 NF. Polysorbates are also available in PhEur grades (European Pharmacopoeia ), BP grades, and JP grades. The term "polysorbate" is a non-proprietary name. The chemical name of polysorbate 20 is polyoxyethylene 20 sorbitan monolaurate. The chemical name of polysorbate 40 is polyoxyethylene 20 sorbitan monopalmitate. The chemical name of polysorbate 60 is polyoxyethylene 20 sorbitan monostearate. The chemical name of polysorbate 80 is polyoxyethylene 20 sorbitan monooleate. In some embodiments, the composition, carrier, and/or diluent can comprise mixtures of polysorbates. In some embodiments, the composition, carrier, and/or diluent comprises polysorbate 20, polysorbate 40, polysorbate 60, polysorbate 65, polysorbate 80, polysorbate 85, and/or polysorbate 120. In some embodiments, the composition, carrier, and/or diluent comprises polysorbate 20, polysorbate 40, polysorbate 60, and/or polysorbate 80. In one embodiment, the composition, carrier, and/or diluent comprises polysorbate 80.

In some embodiments, the composition, carrier, and or diluent can comprise an alcohol, such as ethanol. The ethanol can be USP grade such as Alcohol USP or Dehydrated Alcohol (200 proof) USP. In some embodiments, the composition comprises taxane particles, a carrier, and optionally a diluent, wherein the carrier and/or diluent comprises water, ethanol, and a polysorbate. In some embodiments, the ethanol is present in the composition, carrier, and or diluent at a concentration of about 0.1% w/v to about 10% w/v, or about 0.1% w/v to about 8% w/v, or about 2% w/v to about 8% w/v, or about 5% w/v to about 10% w/v, or about 8% w/v. In some embodiments, the ethanol is present in the composition at a concentration of about 0.1 w/v to about 4% w/v, or about 2% w/v to about 4% w/v, or about 3.2% w/v.

In some embodiments, the composition comprises antineoplastic particles, a carrier, and optionally a diluent, wherein the carrier and/or diluent comprises water and a polysorbate. In one embodiment, the composition is a suspension, the antineoplastic particles are taxane particles, and the polysorbate is polysorbate 80. In other embodiments, the polysorbate or polysorbate 80 is present in the composition, carrier, and or diluent at a concentration of between about 0.01% v/v and about 1.5% v/v. The inventors have surprisingly discovered that the recited very small amounts of polysorbate 80 reduce the surface tension at the interface of the antineoplastic particles and the aqueous carrier (such as saline solution). These embodiments are typically formulated near the time of use of the composition. In some embodiments, the particles may be coated with the polysorbate or polysorbate 80. In other embodiments, the particles are not coated with the polysorbate or polysorbate 80. In various other embodiments the polysorbate or polysorbate 80 is present in the composition, carrier, and/or diluent at a concentration of between, about 0.01% v/v and about 1% v/v, about 0.01 % v/v and about 0.5% v/v, about 0.01% v/v and about 0.4% v/v, about 0.01% v/v and about 0.35% v/v, about 0.01% v/v and about 0.3% v/v, about 0.01% v/v and about 0.25% v/v, about 0.01% v/v and about 0.2% v/v, about 0.01% v/v and about 0.15% v/v, about 0.01% v/v and about 0.1% v/v, about 0.05% v/v and about 1% v/v, about 0.05% v/v and about 0.5% v/v, about 0.05% v/v and about 0.4% v/v, about 0.05% v/v and about 0.35% v/v, about 0.05%. v/v and about 0.3% v/v, about 0.05% v/v and about 0.25% v/v, about 0.05% v/v and about 0.2% v/v, about 0.05% v/v and about 0.15% v/v, about 0.05% v/v and about 0.1% v/v, about 0.1 % v/v and about 1% v/v, about 0.1% v/v and about 0.5% v/v, about 0.1% v/v and about 0.4% v/v, about 0.1% v/v md about 0.35% v/v, about 0.1% v/v and about 0.3% v/v, about 0.1% v/v and about 0.25% v/v, about 0.1% v/v and about 0.2% v/v, about 0.1% v/v and about 0.15% v/v, about 0.2% v/v and about 1 % v/v, about 0.2% v/v and about 0.5% v/v, about 0.2% v/v and about 0.4% v/v, about 0.2% v/v and about 0.35% v/v, about 0.2% v/v and about 0.3% v/v, about 0.2% v/v and about 0.25% v/v, about 0.3% v/v and about 1% v/v, about 0.3% v/v and about 0.5% v/v, about 0.3% v/v and about 0.4% v/v, or about 0.3% v/v and about 0.35% v/v; or about 0.01%, about 0.05%, about 0.1% v/v, about 0.15% v/v, about 0.16% v/v, about 0.2% v/v, about 0.25% v/v, about 0.3% v/v, about 0.35% v/v, about 0.4% v/v, about 0.45% v/v, about 0.5% v/v, or about 1% v/v.

The composition, carrier, and/or diluent can comprise one or more tonicity adjusting agents. Suitable tonicity adjusting agents include by way of example and without limitation, one or more inorganic salts, electronics, sodium chloride, potassium chloride, sodium phosphate, potassium phosphate, sodium, potassium sulfates, sodium and potassium bicarbonates and alkaline earth metal salts, such as alkaline earth metal inorganic salts, e.g., calcium salts, and magnesium salts, mannitol, dextrose, glycerin, propylene glycol, and mixtures thereof.

The composition, carrier, and/or diluent can comprise one or more buffering agents. Suitable buffering agents include by way of example and without limitation, dibasic sodium phosphate, monobasic sodium phosphate, citric acid, sodium citrate, tris(hydroxymethyl)aminomethane, bis(2-hydroxyethyl)iminotris-(hydroxymethyl)methane, and sodium hydrogen carbonate and others known to those of ordinary skill in the art. Buffers are commonly used to adjust the pH to a desirable range for intraperitoneal use. Usually a pH of around 5 to 9, 5 to 8,6 to 7.4,5.5 to 7.5, or 6.9 to 7.4 is desired.

The composition, carrier, and/or diluent can comprise one or more demulcents. A demulcent is an agent that forms a soothing film over a mucous membrane, such as the membranes lining the peritoneum and organs therein. A demulcent may relieve minor pain and inflammation and is sometimes referred to as a mucoprotective agent. Suitable demulcents include cellulose derivatives ranging from about 0.2 to about 2.5 % such as carboxymethylcellulose sodium, hydroxyethyl cellulose, hydroxypropyl methylcellulose, and methylcellulose; gelatin at about 0.01%; polyols in about 0.05 to about 1%, also including about 0.05 to about 1%, such as glycerin, polyethylene glycol 300, polyethylene glycol 400, and propylene glycol; polyvinyl alcohol from about 0.1 to about 4 %; povidone from about 0.1 to about 2%; and dextran 70 from about 0.1% when used with another polymeric demulcent described herein.

The composition, carrier, and/or diluent can comprise one or more alkalinizing agents to adjust the pH. As used herein, the term "alkalizing agent" is intended to mean a compound used to provide an alkaline medium. Such compounds include, by way of example and without limitation, ammonia solution, ammonium carbonate, potassium hydroxide, sodium carbonate, sodium bicarbonate, and sodium hydroxide and others known to those of ordinary skill in the art.

The composition, carrier, and or diluent can comprise one or more acidifying agents to adjust the pH. As used herein, the term "acidifying agent" is intended to mean a compound used to provide an acidic medium. Such compounds include, by way of example and without limitation, acetic acid, amino acid, citric acid, nitric acid, fumaric acid and other alpha hydroxy acids, hydrochloric acid, ascorbic acid, and nitric acid and others known to those of ordinary skill in the art.

The composition, carrier, and/or diluent can comprise one or more antifoaming agents. As used herein, the term "antifoaming agent" is intended to mean a compound or compounds that prevents or reduces the amount of foaming that forms on the surface of the fill composition. Suitable antifoaming agents include by way of example and without limitation, dimethicone, SIMETHICONE, octoxynol and others known to those of ordinary skill in the art.

The composition, carrier, and or diluent can comprise one or more viscosity modifiers that increase or decrease the viscosity of the suspension. Suitable viscosity modifiers include methylcellulose, hydroxypropyl methycellulose, mannitol, polyvinylpyrrolidone, cross-linked acrylic acid polymers such as carbomer, and others known to those of ordinary skill in the art. The composition, carrier, and/or diluent can further comprise theology modifiers to modify the flow characteristics of the composition to allow it to adequately flow through devices such as injection needles or tubes. Non-limiting examples of viscosity and rheology modifiers can be found in "Rheology Modifiers Handbook—Practical Use and Application" Braun, William Andrew Publishing, 2000.

The concentration or amount of antineoplastic particles in the composition or dosage is at an "effective amount", i.e., to provide a therapeutic effect on an epithelial cyst of a subject by accomplishing one or more of the following: (a) reducing cyst volume/size; (b) reducing cyst growth rate; (c) eliminating a cyst; (d) ablation of a cyst or (e) reducing pain associated with the cyst. In one embodiment, the concentration of the antineoplastic particles, which can be taxane particles, in the composition is between about 0.1 mg/mL and about 100 mg/mL. In various further embodiments, the concentration of antineoplastic particles, which can be taxane particles, in the composition is between: about 0.5 mg/mL and about 100 mg/mL, about 1 mg/mL and about 100 mg/mL, about 2 mg/mL and about 100 mg/mL, about 5 mg/mL and about 100 mg/mL, about 10 mg/mL and about 100 mg/mL, about 25 mg/mL and about 100 mg/mL, about 30 mg/mL and about 100 mg mL, about 0.1 mg/mL and about 75 mg/mL, about 0.5 mg/mL and about 75 mg/mL, about 1 mg/mL and about 75 mg/mL, about 2 mg/mL and about 75 mg/mL, about 5 mg/mL and about 75 mg/mL, about 10 mg/mL and about 75 mg/mL, about 25 mg/mL and about 75 mg/mL, about 30 mg/mL and about 75 mg/mL, about 0.1 mg/mL and about 50 mg mL, about 0.5 mg/mL and about 50 mg/mL, about 1 mg/mL and about 50 mg/mL, about 2 mg/mL and about 50 mg/mL, about 5 mg/mL and about 50 mg/mL, about 10 mg/mL and about 50 mg/mL, about 25 mg/mL and about 50 mg/mL, about 30 mg/mL and about 50 mg/mL, about 0.1 mg/mL and about 40 mg/mL, about 0.5 mg/mL and about 40 mg/mL, about 1 mg/mL and about 40 mg/mL, about 2 mg/mL and about 40 mg/mL, about 5 mg/mL and about 40 mg/mL, about 10 mg/mL and about 40 mg/mL, about 25 mg/mL and about 40 mg/mL, about 30 mg/mL and about 40 mg/mL, about 0.1 mg/mL and about 30 mg/mL, about 0.5 mg/mL and about 30 mg/mL, about 1 mg/mL and about 30 mg/mL, about 2 mg/mL and about 30 mg/mL, about 5 mg/mL and about 30 mg/mL, about 10 mg/mL and about 30 mg/mL, about 25 mg/mL and about 30 mg/mL, about 0.1 mg/mL and about 25 mg/mL, about 0.5 mg/mL and about 25 mg/mL, about 1 mg/mL and about 25 mg/mL, about 2 mg/mL and about 25 mg/mL, about 5 mg/mL and about 25 mg/mL, about 10 mg/mL and about 25 mg/mL, about 0.1 mg/mL and about 20 mg/mL, about 0.5 mg/mL and about 20 mg/mL, about 1 mg/mL and about 20 mg/mL, about 2 mg/mL and about 20 mg/mL, about 5 mg/mL and about 20 mg/mL, about 10 mg/mL and about 20 mg/mL, about 0.1 mg/mL and about 15 mg/mL, about 0.5 mg/mL and about 15 mg/mL, about 1 mg/mL and about 15 mg/mL, about 2 mg/mL and about 15 mg/mL, about 5 mg/mL and about 15 mg/mL, about 10 mg/mL and about 15 mg/mL, about 0.1 mg/mL and about 10 mg/mL, about 0.5 mg/mL and about 10 mg/mL, about 1 mg/mL and about 10 mg/mL, about 2 mg/mL and about 10 mg/mL, about 5 mg/mL and about 10 mg/mL, about 0.1 mg/mL and about 5 mg/mL, about 0.5 mg/mL and about 5 mg/mL, about 1 mg/mL and about 5 mg/mL, about 2 mg/mL and about 5 mg/mL, about 0.1 mg/mL and about 2 mg/mL, about 0.5 mg/mL and about 2 mg/mL, about 1 mg/mL and about 2 mg/mL, about 0.1 mg/mL and about 1 mg/mL, about 0.5 mg/mL and about 1 mg/mL, about 0.1 mg/mL and about 0.5 mg/mL, about 3 mg/mL and about 8 mg/mL, or about 4 mg/mL and about 6 mg/mL; or at least about 0.1, 0.5, 1, 2, 3, 4, 5, 6, 7, 8, 9, 10, 11, 12, 13, 14, 15, 16, 17, 18, 19, 20, 25, 30, 35, 40, 45, 50, 55, 60, 61, 65, 70, 75, or 100 mg/mL; or about 0.1, 0.5, 1, 2, 3, 4, 5, 6, 7, 8, 9, 10, 11, 12, 13, 14, 15, 16, 17, 18, 19, 20, 25, 30, 35, 40, 41, 42, 43, 44, 45, 46, 47, 48, 49, 50, 55, 60, 61, 65, 70, 75, or 100 mg/mL. The antineoplastic particles may be the sole therapeutic agent administered, or may be administered with other therapeutic agents.

In various embodiments, the composition comprises taxane particles (paclitaxel particles or docetaxel particles), a carrier, and a diluent, wherein the concentration of taxane particles in the composition (including the carrier and diluent) is between: about 1 mg/mL and about 40 mg/mL, about 5 mg/mL and about 20 mg/mL, about 5 mg/mL and about 15 mg/mL, about 5 mg/mL and about 10 mg/mL, about 6 mg/mL and about 20 mg/mL, about 6 mg/mL and about 15 mg/mL, about 6 mg/mL and about 10 mg/mL, about 10 mg/mL and about 20 mg/mL, or about 10 mg/mL and about 15 mg/mL; or about 6 mg/mL, about 10 mg/mL, or about 15 mg/mL. In further embodiments, the carrier is an aqueous carrier which can be saline solution, such as about 0.9% sodium chloride solution and the diluent is an aqueous diluent which can be saline solution, such as about 0.9% sodium chloride solution. In further embodiments, the aqueous carrier comprises a polysorbate, such as polysorbate 80.

The compositions should be at suitable volume to supply a sufficient dose volume for intracystic injections, i.e., where the volume of the dose is equal to the amount of cyst fluid withdrawn from the cyst prior to injection. Thus, the volume of the composition should be equal to or greater than the dose volume. The volume of withdrawn cyst fluid can vary depending on the type of cyst. Generally, the volume of cyst fluid removed from pancreatic cysts is about 2 to about 10 mL, and typically is about 4 to about 5 mL. In some embodiments, the volume of the composition is sufficient to provide a dose volume of about 2 to about 10 mL, or about 4 to about 5 mL.

In some embodiments, the volume of the composition is: 10 ul-60 mL, 10 ul-50 mL, 10 ul-40 mL, 10 ul-35 mL, 10 ul-30 mL, 10 ul-25 mL, 10 ul-20 mL, 10 ul-15 mL, 10 ul-10 mL, 10 ul-7.5 mL, 10 ul-7 mL, 10 ul-5 mL, 10 ul-4 mL, 10 ul-3 mL, 50 ul-60 mL, 50 ul-50 mL, 50 ul-40 mL, 50 ul-35 mL, 50 ul-30 mL, 50 ul-25 mL, 50 ul-20 mL, 50 ul-15 mL, 50 ul-10 mL, 50 ul-7.5 mL 50 ul-7 mL, 50 ul-5 mL, 50 ul-4 mL, 50 ul-3 mL, 100 ul-60 mL, 100 ul-50 mL 100 ul-40 mL, 100 ul-35 mL, 100 ul-30 mL, 100 ul-25 mL, 100 ul-20 mL, 100 ul-15 mL, 100 ul-10 mL, 100 ul-7.5 mL, 100 ul-7 mL, 100 ul-5 mL, 100 ul-4 mL, 100 ul-3 mL, 500 ul-60 mL, 500 ul-50 mL, 500 ul-40 mL, 500 ul-35 mL, 500 ul-30 mL, 500 ul-25 mL, 500 ul-20 mL, 500 ul-15 mL, 500 ul-10 mL, 500 ul-7.5 mL, 500 ul-7 mL, 500 ul-5 mL, 500 ul-4 mL, 500 ul-3 mL, 1 mL-60 mL, 1 mL-50 mL 1 mL-40 mL, 1 mL-35 mL, 1 mL-30 mL, 1 mL-25 mL, 1 mL-20 mL, 1 mL-15 mL, 1 mL-12 mL, 1 mL -10 mL, 1 mL-7.5 mL, 1 mL-7 mL, 1 mL-5 mL, 1 mL-4 mL, or 1 mL-3 mL. In some embodiments, the volume of the composition is about: 1 mL, 2 mL, 3 mL, 4, mL, 5 mL, 6, mL, 7 mL, 8, mL, 9 mL, 10 mL, 12 mL, 15, mL, 20 mL, 30 mL, 40, mL, 50 mL, or 60 mL. Thus, in another aspect, the invention provides pharmaceutical compositions comprising antineoplastic particles or taxane particles and a pharmaceutically acceptable carrier, where the total volume of the composition is between: 1 mL and 60 mL, 1 mL and 50 mL, 1 mL and 40 mL, 1 mL and 35 mL, 1 mL and 30 mL, 1 mL and 25 mL, 1 mL and 20 mL, 1 mL and 15 mL, 1 mL and 12 mL, 1 mL and 10 mL, 1 mL and 7.5 mL, 1 mL and 7 mL, 1 mL and 5 mL, 1 mL and 4 mL, or 1 mL and 3 mL.

Kits

The present invention also provides kits, comprising.
(a) a first vial comprising, consisting essentially of, or consisting of antineoplastic particles;
(b) a second vial comprising a pharmaceutically acceptable carrier; and
(c) instructions for reconstituting the antineoplastic particles into a suspension useful tor intracystic injection by: combining the contents of the first vial and the second vial to form the suspension and optionally diluting the suspension with a diluent.

In preferred embodiments, the antineoplastic particles are taxane particles such as paclitaxel particles or docetaxel particles. The antineoplastic particles in the first vial can be in a powder form. The antineoplastic particles in the first vial can be the sole ingredient in the first vial. In some embodiments, the taxane particles have a mean particle size (number) of from 0.1 microns to 1.5 microns. The pharmaceutically acceptable carrier can be an aqueous carrier such as 0.9% saline solution. The carrier can further comprise a surfactant such as a polysorbate. In some embodiments, the polysorbate is polysorbate 80. In some embodiments, the polysorbate or polysorbate 80 is at a concentration of between about 0.01% v/v and about 1% v/v. In some embodiments, the taxane particles are paclitaxel particles and have a specific surface area (SSA) of at least 18 $m^2/g$ and/or a bulk density (not-tapped) of 0.05 $g/cm^3$ to 0.15 $g/cm^3$. In other embodiments, the taxane particles are docetaxel particles and have a specific surface area (SSA) of at lean 18 $m^2/g$ and/or a bulk density (not-tapped) of 0.05 $g/cm^3$ to 0.15 $g/cm^3$. When the suspension of antineoplastic particles and carrier containing a polysorbate is diluted with the diluent, excessive dissolution of the antineoplastic particles is prevented.

Any suitable vial can be used in the kits. A non-limiting example of a suitable vial is a Type 1, USP, clear-glass vial closed with a bromobutyl rubber stopper and aluminum crimp seal. The volumes of the vials can vary depending on the amount of antineoplastic particles, the volume of the carrier, and the volume of the final reconstituted suspension. The vials and their contents can be sterilized using sterilization methods known in the art such as gamma irradiation or autoclaving. In some embodiments, the contents of the vials are sterile. The kits can be configured for single-dose or multiple-dose administration.

A non-limiting exemplary procedure for preparing a suspension composition from a kit is as follows:
1. Using a syringe with a suitable gauge needle, add all or a portion of the carrier from the second vial into the first vial containing the anti-neoplastic particles.
2. Vigorously hand shake the first vial with inversions to make sure all the particles adhering to the interior of the vial and stopper are wetted.
3. Continue shaking tor 1 minute and examine the suspension for any large clumps of particles.
4. Immediately after shaking, use a syringe with a suitable gauge needle to add a prescribed volume of a diluent to the first vial to dilute the suspension to a desired dose level, and hand shake the vial for another 1 minute. Periodically examine the suspension for any large visible clumps. If present, continue hand mixing until the suspension is properly dispersed.
5. After mixing, allow the suspension to sit undisturbed for at least 5 minutes to reduce entrapped air and foam.

The compositions, suspensions, and kits of the invention can include any embodiment or combination of embodiments described herein including any embodiments of the antineoplastic particles, any embodiments of the carriers and diluents, and any embodiments of the polysorbate or polysorbate 80 concentrations. The compositions, suspensions, and kits can exclude polymers, proteins (such as albumin), polyethoxylated castor oil, and/or polyethylene glycol glycerides composed of mono-, di- and triglycerides and mono and diesters of polyethylene glycol. The compositions and kits can further comprise other components as appropriate for given antineoplastic particles.

Methods of Administration/Treatment

The compositions comprising antineoplastic particles, including taxane particles, described and disclosed supra can be used in methods for the treatment of epithelial cystic neoplasms (cysts) in subjects by direct injection of the compositions into the cysts (intracystic injection). Epithelial cysts are cysts which have an epithelial inner lining. The compositions and methods disclosed herein are useful for treatment of any type of epithelial cyst. Non-limiting examples of epithelial cysts include gastrointestinal cysts such as hepatic cysts, pancreatic cysts, splenic cysts, colon cysts; urologic cysts such as renal cysts, epididymal cysts, prostatic cysts; gynecological cysts such as ovarian cysts and vaginal cysts; head and neck cysts such as thyroid cysts, parathyroid cysts, and other head and neck cysts; as well as other cysts such as Baker's cysts, lung cysts, lymphatic cysts, and pericardial cysts. In some embodiments, the epithelial cyst is a pancreatic cyst. A pancreatic cyst can be an intraductal papillary mucinous neoplasm (IPMN), a mucinous cystic neoplasms (MCN), or a serous cystadenoma. In some embodiments, the pancreatic cyst is an intraductal papillary mucinous neoplasm (IPMN). In other embodiments, the pancreatic cyst is a mucinous cystic neoplasms (MCN). In still other embodiments, the pancreatic cyst is a serous cystadenoma.

The injection of the composition into an epithelial cyst can be conducted by use of a procedure known as "endoscopic ultrasound-guided fine needle injection" (EUS-FNI), which is a procedure in which endoscopy is combined with ultrasound to aid in the location of the cyst and to facilitate the injection of the composition into the cyst. Because the antineoplastic particles are solid particles, the suspensions of antineoplastic particles can be more easily visualized with sonography than solutions of antineoplastic agents or even suspensions of albumin coated particles. This is especially evident when the antineoplastic particles are in crystalline form. This feature provides a tremendous advantage in that the flow and volume of the suspension can easily be seen during the procedure and can be regulated by the administrator so that no stress is put onto the cyst by overfilling resulting in the suspension being pushed out of the cyst due to lack of space. Thus, in another aspect of the invention, disclosed are methods of administering a composition comprising antineoplastic particles to an epithelial cyst of a subject, the method comprising injecting the particles using endoscopic ultrasound guided-fine needle injection. This procedure is also applicable to injection into solid tumors such as malignant tumors. In some embodiments, the antineoplastic particles have a mean particle size (number) of from 0.1 microns to 5 microns. In other embodiments, the antineoplastic particles have a mean particle size (number) of from 0.3 microns to 5 microns. In preferred embodiments, the antineoplastic particles are crystalline particles. In some embodiments, the antineoplastic particles are taxane particles. In some embodiments, the taxane particles comprise at least 95% of the taxane. In some embodiments, the taxane particles exclude albumin. In some embodiments, the taxane particles are paclitaxel particles or docetaxel particles.

A non-limiting exemplary procedure for injection of the composition into a pancreatic cyst is as follows: a linear array echcoendoscope is inserted via the mouth and advanced to the stomach or duodenum, whichever provides the best access to the cyst. A 22-gauge fine needle aspiration (FNA) needle is luer locked into the accessory channel of the echoendoscope. The needle tip is maintained in the cyst for the duration of the procedure. Using a syringe, the cyst fluid is aspirated from the cyst (usually up to 80% of the original volume of the cyst, but more than 80% of the cyst fluid can be aspirated). The volume of cyst fluid withdrawn is determined. The needle is then filled with the composition, and is injected directly into the cyst. The volume of the composition injected into the cyst can be at a volume equal to the volume of cyst fluid aspirated.

The methods can further comprise additional treatments such as cyst fluid aspiration by endoscopic ultrasound-guided fine needle aspiration (EUS-FNA) performed before the intracystic injection procedure as stated above.

The epithelial cyst is successfully treated when the cyst is reduced in volume/size, has reduced growth rate, is eliminated, or is ablated after treatment by intracystic injection of the composition.

EXAMPLES

The present invention will be described in greater detail by way of specific examples. The following examples are offered for illustrative purposes only, and are not intended to limit the invention in any manner. Those of skill in the art will readily recognize a variety of noncritical parameters, which can be changed or modified to yield essentially the same results.

Example 1. Production of Paclitaxel Particles and Docetaxel Particles

Materials and Methods

Raw paclitaxel and docetaxel were purchased from Phyton Biotech (British Columbia, Canada), lot number FP2-15004 and DT7-14025, respectively. Both were characterized in their raw form. The milling of both drugs was accomplished using a Deco-PBM-V-0.41 mill (Deco). The milling conditions for both compounds were as follows:
 Ball size=5 mm
 RPM=600
 Processing time=60 min
 Room temperature.

Preparation of Paclitaxel Particles

A solution of 65 mg/mL of paclitaxel was prepared in acetone. A BETE MicroWhirl® fog nozzle (BETE Fog Nozzle, Inc) and a sonic probe (Qsonica, model number Q700) were positioned in the crystallization clamber approximately 8 mm apart A stainless steel mesh filter with approximately 100 nm holes was attached to the crystallization chamber to collect the precipitated paclitaxel nanoparticles. The supercritical carbon dioxide was placed in the crystallization chamber of the manufacturing equipment and brought to approximately 1200 psi at about 38° C. and a flow rate of 24 kg/hour. The sonic probe was adjusted to 60% of total output power at a frequency of 20 kHz. The acetone solution containing the paclitaxel was pumped through the nozzle at a flow rate of 4.5 mL/minute for approximately 36 hours. Paclitaxel nanoparticles produced had an average number-weighted mean size of 0.81 μm with an average standard deviation of 0.74 μm over three separate runs.

Preparation of Docetaxel Particles

A solution of 79.32 mg/mL of docetaxel was prepared in ethanol. The nozzle and a sonic probe were positioned in the pressurizable chamber approximately 9 mm apart. A stainless steel mesh filter with approximately 100 nm holes was attached to the pressurizable chamber to collect the precipitated docetaxel nanoparticles. The supercritical carbon dioxide was placed in the pressurizable chamber of the manufacturing equipment and brought to approximately 1200 psi at about 38° C. and a flow rate of 68 slpm. The sonic probe was adjusted to 60% of total output power at a frequency of 20 kHz. The ethanol solution containing the docetaxel was pumped through the nozzle at a flow rate of 2 mL/minute for approximately 95 minutes). The precipitated docetaxel agglomerates and particles were then collected from the supercritical carbon dioxide as the mixture is pumped through the stainless steel mesh filter. The filter containing the nanoparticles of docetaxel was opened and the resulting product was collected from the filter.

Docetaxel nanoparticles produced had an average number-weighted mean size of 0.82 μm with an average standard deviation of 0.66 μm over three separate ethanol runs.

Particle Size Analysis

Particle size was analyzed by both light obscuration and laser diffraction methods. An Particle Sizing Systems AccuSizer 780 SIS system was used for the light obscuration method and Shimadzu SALD-7101 was used for the laser diffraction method. Paclitaxel nanoparticles were analyzed using 0.10% (w/v) sodium dodecyl sulfate (SDS) in water as the dispersant. Docetaxel nanoparticles were analyzed using isopar G as the dispersant.

Paclitaxel suspensions were prepared by adding approximately 7 mL of filtered dispersant to a glass vial containing approximately 4 mg of paclitaxel particles. The vials were vortexed for approximately 10 seconds and then sonicated in a sonic bath approximately 1 minute. If the sample was already suspended, 1:1 solution of paclitaxel suspension to 0.1% SDS solution was made, vortexed for 10 seconds, and sonicated in the sonic bath for 1 minute.

Docetaxel suspensions were prepared by adding approximately 7 mL of filtered dispersant to a plastic vial containing approximately 4 mg of docetaxel particles. The vial was vortexed for approximately 10 seconds and then sonicated in a sonic bath for approximately 2 minutes. This suspension was used for laser diffraction analysis. Unused suspension was poured into a 125 mL particle-free plastic bottle, which was then filled to approximately 100 mL with filtered dispersant. The suspension was vortex for approximately 10 seconds and then sonicated in the sonic bath for approximately 2 minutes. This diluted suspension was used for light obscuration analysis.

A background test was first performed prior to analyzing particles on the AccuSizer 780 SIS. A new particle-free plastic bottle was filled with blank suspension solution by pumping from a reservoir, using a peristaltic pump, through a 0.22 μm Millipore filter and into the bottle. A background analysis was run to ensure the particle/mL count was below 100 particles/mL. A small amount of paclitaxel suspension, 5-100 μL, depending upon concentration of solution, was pipetted into the plastic bottle in place from the background test and was filled with ~100 mL dispersant and the analysis was started. Counts were monitored and paclitaxel solution added to reach and/or maintain 6000-8000 particle counts/mL during the entire analysis. Once the analysis was completed, the background data was removed and any measurement with less than four counts was removed.

To analyze particles on SALD-7101 using a batch cell, the analysis was started by choosing Manual Measurement. The refractive index was set as 1.5 to 1.7. The batch cell was filled with filtered dispersant just past the etched line. The blank measurement was ran. A small amount of API (paclitaxel or docetaxel) suspension was pipetted, generally <1 mL, depending upon concentration of solution as low as 100 μL, into the batch cell as needed to achieve an acceptable absorbance between 0.15 and 0.2 absorbance units. The measurements were executed, and the resulting graph with the highest level of confidence was selected; background was automatically accounted for.

BET Analysis

A known mass between 200 and 300 mg of the analyte was added to a 30 mL sample tube. The loaded tube was then mounted to a Porous Materials Inc. SORPTOMETER®, model BET-202A. The automated test was then carried out using the BETWIN® software package and the surface area of each sample was subsequently calculated.

Bulk Density Analyte

Paclitaxel or docetaxel particle preparations were added to a 10 mL tared graduated cylinder through a plastic weigh funnel at room temperature. The mass of the drug was measured to a nearest 0.1 mg, the volume was determined to the nearest 0.1 mL and the density calculated.

Dissolution Studies

Paclitaxel

Approximately 50 mg of material (i.e.: raw paclitaxel, milled paclitaxel, or paclitaxel particles) were coated on approximately 1.5 grams of 1 mm glass beads by tumbling the material and beads in a vial for approximately 1 hour. Beads were transferred to a stainless steel mesh container and placed in the dissolution bath containing methanol/water 50/50 (v/v) media at 37° C., pH 7, and a USP Apparatus II (Paddle), operating at 75 rpm. At 10, 20, 30, 60, and 90 minutes, a 5 mL aliquot was removed, filtered through a 0.22 μm filter and analyzed on a U(V/V)is spectrophotometer at 227 nm. Absorbance values of the samples were compared to those of standard solutions prepared in dissolution media to determine the amount of material dissolved.

Docetaxel

Approximately 50 mg of material (i.e.: raw docetaxel, milled docetaxel, or docetaxel particles) was placed directly in the dissolution bath containing methanol/water 15/85 (v/v) media at 37° C., pH 7, and a USP Apparatus II (Paddle), operating at 75 rpm. At 5, 15, 30, 60, 120 and 225 minutes, a 5 mL aliquot was removed, filtered through a 0.22 μm filter, and analyzed on a UV/VIS spectrophotometer at 232 nm. Absorbance values of the samples were compared to those of standard solutions prepared in dissolution media to determine the amount of material dissolved.

Results

The BET surface area of particles produced using the above protocol and variations thereof (i.e.: modifying nozzles, filters, sonic energy sources, flow rates, etc.) ranged between 22 and 39 $m^2/g$. By comparison, the BET surface area of raw paclitaxel was measured at 7.25 $m^2/g$(FIG. 2), while paclitaxel particles made according to the methods of U.S. Pat. Nos. 5,833,891 and 5,874,029 ranged from 11.3 to 15.58 $m^2/g$. Exemplary particle sizes produced using the methods of the invention are shown in Table 1.

TABLE 1

| | Surface area | Mean Size μm | | St Dev μm | |
|---|---|---|---|---|---|
| | $m^2/g$ | Number | Volume | Number | Volume |
| 1 | 38.52 | 0.848 | 1.600 | 0.667 | 0.587 |
| 2 | 33.82 | 0.754 | 0.988 | 0.536 | 0.486 |
| 3 | 35.90 | 0.777 | 1.259 | 0.483 | 0.554 |
| 4 | 31.70 | 0.736 | 0.953 | 0.470 | 0.466 |
| 5 | 32.59 | 0.675 | 0.843 | 0.290 | 0.381 |
| 6 | 38.22 | 0.666 | 0.649 | 0.344 | 0.325 |
| 7 | 30.02 | 0.670 | 0.588 | 0.339 | 0.315 |
| 8 | 31.16 | 0.672 | 0.862 | 0.217 | 0.459 |
| 9 | 23.90 | 0.857 | 1.560 | 0.494 | 0.541 |
| 10 | 22.27 | 0.857 | 1.560 | 0.494 | 0.541 |
| 11 | 26.19 | 0.861 | 1.561 | 0.465 | 0.546 |

Comparative studies on bulk density. SSA, and dissolution rates (carried out as noted above) for raw drug, milled drug particles, and drug particles produced by the methods of the present invention are provided in Tables 2 and 3 below. The full dissolution time course for the paclitaxel and docetaxel materials are provided in Tables 4 and 5, respectively.

TABLE 2

| | Compound: Paclitaxel | | | | |
|---|---|---|---|---|---|
| | Raw | Particles | | | |
| Characteristic | Material | Batch 1 | Batch 2 | Mean | Milled |
| Number Mean (μm) | 1.16 | 0.83 | 0.67 | 0.75 | 0.89 |
| Volume Mean (μm) | 1.29 | 1.42 | 0.57 | 1.00 | 1.35 |
| Bulk Density (g/cm$^3$) | 0.26 | 0.060 | 0.11 | 0.085 | 0.31 |
| Surface Area (m$^2$/g) | 30.4 | 35.6 | 39.8 | 37.7 | 15.0 |
| Dissolution (30 min) | 18% | 42% | 52% | 47% | 32% |

TABLE 3

| | Compound: Docetaxel | | | | |
|---|---|---|---|---|---|
| | Raw | Particles | | | |
| Characteristic | Material | Batch 1 | Batch 2 | Mean | Milled |
| Number Mean (µm) | 1.58 | 0.92 | 0.80 | 0.86 | 1.11 |
| Volume Mean (µm) | 5.05 | 4.88 | 4.03 | 4.46 | 3.73 |
| Bulk Density (g/cm$^3$) | 0.24 | 0.062 | 0.096 | 0.079 | 0.44 |
| Surface Area (m$^2$/g) | 15.9 | 43.0 | 45.4 | 44.2 | 15.2 |
| Dissolution (30 min) | 11% | 27% | 27% | 27% | 9% |

TABLE 4

Paclitaxel Dissolution time course

| Timepoint (minutes) | Paclitaxel Raw Material | Paclitaxel Particles | Milled Paclitaxel |
|---|---|---|---|
| 0 | 0.0% | 0.0% | 0.0% |
| 10 | 14.0% | 40.2% | 23.0% |
| 20 | 17.8% | 47.6% | 30.0% |
| 30 | 18.4% | 51.9% | 32.3% |
| 60 | 23.9% | 58.3% | 38.6% |
| 90 | 28.6% | 62.9% | 43.5% |

TABLE 5

Docetaxel Dissolution time course

| Timepoint (minutes) | Paclitaxel Raw Material | Paclitaxel Particles | Milled Paclitaxel |
|---|---|---|---|
| 0 | 0.0% | 0.0% | 0.0% |
| 5 | 3.2% | 12.1% | 3.2% |
| 15 | 6.9% | 21.7% | 5.9% |
| 30 | 11.2% | 27.2% | 9.3% |
| 60 | 16.4% | 32.9% | 12.2% |
| 20 | 22.4% | 38.9% | 13.6% |
| 225 | 26.8% | 43.1% | 16.0% |

Example 2. Phase 2 Study—Intracystic Injection of Paclitaxel Particles in Subjects with Mucinous Cystic Pancreatic Neoplasms Objectives and Purpose of the Study The primary objective of this study was to evaluate the safety and tolerability of paclitaxel particles (referred to as NANOPAC®) injected directly into mucinous cystic pancreatic neoplasms by endoscopic ultrasound-guided fine needle injection (EUS-FNI). Secondary objectives were (a) to describe the PK of NANOPAC when administered into the cyst within the pancreas, and (b) to determine whether any of the NANOPAC dose concentrations (6, 10, or 15 mg/mL) show signs of preliminary efficacy.

Description of the Study Design

In this open-label trial, up to 30 subjects with mucinous cystic pancreatic neoplasms underwent endoscopic ultrasound-guided fine needle aspiration (EUS-FNA) as part of Standard of Care (SOC). Once there was a diagnosis and confirmation of mucinous cystic pancreatic neoplasm, subjects received intracystic NANOPAC via EUS-FNI. Subjects were followed for cyst response to therapy (as shown by imaging) and concentration of paclitaxel in the systemic circulation post-injection (as determined by PK analysis).

Subjects were enrolled in sequential, escalating cohorts of NANOPAC at concentrations of 6, 10, or 15 mg/mL injected directly into the cyst within the pancreas at a volume equivalent to the amount of fluid removed from the cyst. The study included a dose escalation phase and a dose confirmation phase.

Cyst Volume Calculations

If more than one cyst was present in the pancreas of a subject, the Investigator selected a single target cyst and treated only this target cyst. The single target cyst must be a diameter of at least 2 cm but no more than 4 cm; the diameter was measured at the widest point of the cyst. Imaging with magnetic resonance cholangiopancreatography (MRCP), CT scan, or fluorodeoxyglucose-positron emission tomography (FDG-PET) was used to visualize and measure the cyst to confirm subject eligibility and to estimate cyst volume. The same imaging modality used prior to enrollment was repeated at the 3-month and 6-month timepoints. The exact cyst volume calculation was based on measurements performed with endoscopic ultrasound during the NANOPAC injection procedure. Injection volume will be based on, and equal to, the amount of fluid removed from the cyst.

Dose Escalation of Cohorts

Cohorts were enrolled sequentially starring at the lowest dose (6 mg/mL). Each cohort had a planned minimum of three subjects. All data from the first three subjects in a cohort was reviewed and evaluated to determire whether the dose received is considered safe and tolerable, and to determine if dose escalation may occur. The data on the three subjects was reviewed once they had completed the two-week follow-up visit, and the safety and tolerability were assessed, which included reference to dose-limiting toxicities (DLT). A determination was made whether to: (a) escalate to the next dose level cohort (no DLT); (b) add three additional subjects to the current cohort (one DLT); or (c) return to the previous (lower) dose cohort and expand by three subjects (more than one DLT).

The dose most suitable for further evaluation was the highest dose with an acceptable safety and tolerability profile. If one or fewer subjects in a six-subject cohort, or no subjects in a three-subject cohort at the highest dose, experienced a DLT, that cohort was taken into the dose confirmation phase. If greater than one subject in a six-subject cohort experienced a DLT, the previous dose was taken into the dose confirmation phase.

Dose Confirmation Phase

Once the dose deemed appropriate for expansion and further evaluation was determined, additional subjects were enrolled to provide up to a total of 12 subjects dosed at that dose level.

PK Analysis

Plasma samples were taken on the day of injection prior to injection and at 1 and 2 hours after NANOPAC injection, as well as at all other study visits, to characterize the PK of intracystic NANOPAC. Subjects were followed for six months after NANOPAC injection for safety and response to therapy. A further follow-up was conducted at six months.

NANOPAC Study Agent

Paclitaxel particles (referred to as NANOPAC) were presented as a sterilized white powder in a sealed vial within a study kit. The mean particle size (number) of the used in this study was 0.793 microns, the SSA was 29.9 m$^2$/g, the bulk density (not tapped) was 0.0877 g/cm$^3$, and the assay was approximately 100% paclitaxel.

The study agent for all treatment groups was in kits containing: one 60 cc vial of NANOPAC powder, 306 mg per vial, sterile; one vial of Sterile Reconstitution Solution (1% Polysorbate 80, NF in normal saline solution (0.9% Sodium Chloride for Injection, USP)), 7 mL per vial, as a carrier; and one instructions for use (IFU) insert with instructions for reconstitution of the NANOPAC powder in the Sterile Reconstitution Solution to form a suspension and subsequent dilution of the suspension to the required dose (6 mg/mL, 10 mg/mL, or 15 mg/mL) with a diluent. A diluent of normal saline solution (0.9% Sodium Chloride for Injection, USP) will be used. The IFU additionally had instructions for the dose withdrawal procedure. The kits were placed in a carton. The kits were provided for a once-only use and will be assigned to one subject only.

Preparation of the NANOPAC Suspension

The NANOPAC suspension was prepared using the materials supplied in the study agent kit (i.e., one 60 cc vial of NANOPAC powder, 306 mg per vial, sterile; and one vial of Sterile Reconstitution Solution (1% Polysorbate 80, NF in 0.9% Sodium Chloride for Injection, USP), 7 mL per vial, as a earner) plus a diluent of normal saline solution (0.9% Sodium Chloride for Injection, USP), following the procedures below to prepare 3 different dose level suspensions (6 mg/mL, 10 mg/m, and 15 mg/mL):

6 mg/mL NANOPAC in 0.1% Polysorbate 80/0.9% Saline:
1. Using a syringe with an 18-gauge needle or larger, added 5.0 mL of the sterile 1% polysorbate 80 reconstitution solution into the 60 cc NANOPAC powder vial.
2. Vigorously hand shock with inversions to make sure all the particles adhering to the interior of the vial and stopper are wetted.
3. Continued shaking for 1 minute and examined the suspension for any large clumps of particles.
4. Immediately after shaking, used a syringe with an 18-gauge needle or larger to add 46 mL of 0.9% sodium chloride for injection, USP to the vial and hand shook the vial for another 1 minute. Periodically examined the suspension for any large visible clumps. If present, continued hand mixing until the suspension is properly dispersed.
5. After mixing, allowed the suspension to sit undisturbed for at least 5 minutes to reduce entrapped air and foam.

10 mg/mL NANOPAC in 0.16% Polysorbate 80/0.9% Saline:
1. Using a syringe with an 18-gauge needle or larger, added 5.0 mL of the sterile 1% polysorbate 80 reconstitution solution into the 60 cc NANOPAC powder vial.
2. Vigorously hand shook with inversions to make sure all the particles adhering to the interior of the vial and stopper are wetted.
3. Continued shaking for 1 minute and examined the suspension for any large clumps of particles.
4. Immediately after shaking, used a syringe with an 18-gauge needle or larger to add 25.6 mL of 0.9% sodium chloride for injection, USP to the vial and hand shook the vial for another 1 minute. Periodically examined the suspension for any large visible clumps. If present, continued hand mixing until the suspension is properly dispersed.
5. After mixing, allowed the suspension to sit undisturbed for at least 5 minutes to reduce entrapped air and foam.

15 mg/mL NANOPAC in 0.25% Polysorbate 80/0.9% Saline:
1. Using a syringe with an 18-gauge needle or larger, added 5.0 mL of the sterile 1% polysorbate 80 reconstitution solution into the 60 cc NANOPAC powder vial.
2. Vigorously hand shook with inversions to make sure all the particles adhering to the interior of the vial and stopper are wetted.
3. Continued shaking for 1 minute and examined the suspension for any large clumps of particles.
4. Immediately after shaking, used a syringe with an 18-gauge needle or larger to add 15.4 mL of 0.9% sodium chloride for injection, USP to the vial and hand shook the vial for another 1 minute. Periodically examined the suspension for any large visible clumps. If present, continued hand mixing until the suspension is properly dispersed.
5. After mixing, allowed the suspension to sit undisturbed for at least 5 minutes to reduce entrapped air and foam.

After the NANOPAC suspension was fully reconstituted (including final dilution) to the required dose (6, 10, or 15 mg/mL, according to cohort assignment), and at the time of dose administration, a suitable volume for use (based on the cyst size) was withdrawn from the vial into a syringe for use in the administration to the subject.

Dosing and Administration: Intracystic Administration Procedure by Endoscopic Ultrasound-Guided Fine Needle Injection (EUS-FNI)

On the day of NANOPAC administration, the subject received parenteral antibiotic prophylaxis. The subject was positioned in the left lateral decubitus position and was sedated by an anesthesiologist or delegate using monitored anesthesia care (MAC) with or without airway intubation. A linear array echoendoscope was inserted via the mouth and advanced to the stomach or duodenum, whichever provided the best access to the cyst. The cyst was measured using electronic calipers and the size recorded.

The stylet was removed from a 22-gauge line needle aspiration (FNA) needle and the needle was luer locked into tire accessory channel of the echoendoscope. Doppler ultrasound imaging was used to verify lack of intervening vascular structures in the path to the cyst. The needle tip was maintained in the cyst for the duration of the procedure. Using a syringe, the Investigator used their discretion to aspirate the cyst fluid (usually up to 80% of the original volume of the cyst). The volume withdrawn was documented in the source, and a sample was sent for analysis. The needle was then filled with the fully reconstituted NANOPAC suspension from the syringe prepared previously and was injected directly into the cyst at a volume equal to the volume of cyst fluid aspirated. NANOPAC was injected directly into the cyst within the pancreas using endoscope ultrasound guidance.

Starling Dose and Escalation Schedule

NANOPAC was administered in concentrations based on cohort assignment. Investigators administered a volume equal to the volume of cyst fluid aspirated. The first cohort received 6 mg/mL NANOPAC; the second cohort received 10 mg/mL NANOPAC; and the third cohort received 15 mg/mL NANOPAC.

Cohorts were enrolled sequentially starting at the lowest dose (6 mg/mL). Each cohort had a planned minimum of three subjects, each receiving a single dose of the study agent. Escalation to the next cohort proceeded following review of data. Data from the three subjects in a cohort, including all DLT described in this section, was reviewed and evaluated to determine if the dose received was considered safe and tolerable, and to determine if dose escalation may occur. The data on the three subjects was reviewed once they had completed the two-week follow-up visit and assessed safety and tolerability. It was determined whether to: (a) escalate to the next dose level cohort (no DLT); (b) add three additional subjects to the current cohort (one DLT); or (c) return to the previous (lower) dose cohort and expand by three subjects (greater than one DLT). If one or fewer subjects in a six-subject cohort, or no subjects in a three-subject cohort at the highest dose, experienced DLT, that cohort was taken into the Dose Confirmation Phase. If greater than one subject in a six-subject cohort experienced DLT, the previous dose was taken into the Dose Confirmation Phase. A single administration of NANOPAC was injected directly into the cyst within the pancreas.

Endpoints

The primary endpoint was safety aid tolerability, as assessed by adverse event (AE), changes in vital signs, laboratory results, and physical examination at one month following NANOPAC injection. Safety and tolerability was continued to be assessed until the six-month end-of-study visit. The secondary endpoints were (a) Concentration of paclitaxel in the systemic circulation post-injection (as determined by PK analysis), and (b) Cyst volume response (imaging).

Preliminary Results:

Subject 04001: 69-year old woman with a pancreatic cyst of the uncinate process. At time of injection, the widest diameter of the cyst was 2.8 cm. 3.5 mL of 6 mg/mL NanoPac suspension was injected into the cyst to match the quantity of cyst fluid aspirated. At 3-month follow-up, CT scan revealed the cyst had stabilized with the widest diameter remaining at 2.8 cm. At 6-month follow-up, imaging revealed a 3.1×2.3×2.3 cm cyst with a decrease in volume from 10.1 cc to 8.5 cc. No ductal dilation or new focal masses were observed.

Subject 04002: 72-year old woman with a pancreatic cyst. At time of injection, the maximum diameter of the cyst was 2.5 cm. The injection procedure demonstrated that the cyst remained at 2.5 cm, from which 3 mL of cyst fluid was aspirated and 2.5 mL of 6 mg/mL (15 mg total) NanoPac suspension was injected.

Subject 04003: 55-year old woman with a pancreatic cyst at the pancreatic head. A EUS-FNA was performed revealing a cyst of the pancreatic head with a maximum diameter of 2.0 cm, from which 3 mL of cyst fluid was aspirated. 3-months later, the maximum diameter of the cyst had increased from 2.0 cm to 2.7 cm at which time 4 mL of cyst fluid was aspirated and an equal volume of NanoPac suspension (at 6 mg/mL therefore 24 mg total) was injected. At 3-month follow-up, imaging via MRI demonstrated a cyst with a 2.1 cm maximum diameter. Thus, the cyst diameter reduced from 2.7 cm to 2.1 cm in 3 months after the injection of the NanoPac suspension.

Example 3. Intermediate-Size Patient Population Expanded Access of NanoPac® for the Treatment of Mucinous Cystic Pancreatic Neoplasms In this intermediate-size patient population expanded access protocol, up to ten subjects with mucinous cystic pancreatic neoplasms will receive NanoPac suspension injection into the pancreatic cyst following fine needle aspiration, in a volume equal to the volume of fluid removed. Injection will be via endoscopic ultrasound (EUS) following fine needle aspiration of the cyst fluid.

NanoPac (sterile nanoparticulate paclitaxel) powder for suspension is presented as a white powder, 306 mg, provided in a sealed vial within a study kit. The kit will also include one vial of Sterile Reconstitution Solution (1% Polysorbate 80, NF in normal saline solution (0.9% Sodium Chloride for Injection, USP)), and one pre-printed Instructions for Use (IFU) insert in a 2 ct kit. The suspension will be prepared and diluted with normal saline solution and/or lactated Ringer's solution to a concentration of 10 mg/mL suspension and placed into a syringe.

On the day of NanoPac administration, the subject will receive parenteral antibiotic prophylaxis. The subject will be positioned in the left lateral decubitus position and will be sedated by an anesthesiologist or delegate using monitored anesthesia care (MAC) with or without airway intubation. A linear array echoendoscope will be inserted via the mouth and advanced to the stomach or duodenum, whichever provides the best access to the cyst. The cyst will be measured using electronic calipers und the size recorded.

The stylet will be removed from a 22-gauge fine needle aspiration (FNA) needle and the needle will be luer locked into the accessory channel of the echoendoscope. Doppler ultrasound imaging will be used to verify lack of intervening vascular structures in the path to the cyst. The needle lip will be maintained in the cyst for the duration of the procedure. Using a syringe, the Investigator will use their discretion to aspirate the cyst fluid (usually up to 80% of the original volume of the cyst). The volume withdrawn will be documented in the source, and a sample will be sent for analysis. The needle will then be filled with the study treatment, NanoPac, from the syringe, and NanoPac will be injected at a volume equal to the volume of cyst fluid aspirated.

During the immediate follow-up period (first two weeks) review of safety and possible paclitaxel-related toxicities will be evaluated, and further follow up will be as per standard of care and will include imaging at 3 and 6 months post NanoPac injection.

Example 4. In-vitro Release Testing Study. Comparative Measurements of Paclitaxel and Docetaxel Concentration Equilibration Across Natural and Synthetic Membranes An in-vitro release testing study was conducted to comparatively measure the flux of formulations of various forms of paclitaxel and docetaxel across natural epithelial membranes.

Test Articles:

NanoPac (nanoparticulate paclitaxel powder, approximately 98% paclitaxel with a mean particle size (number) of 0.827 microns, a SSA of 27.9 $mg^2/g$, and a bulk density (not tapped) of 0.0805 $g/cm^3$ used in this example) in Suspension, 6 mg/mL.

NanoDoce (nanoparticulate docetaxel powder, approximately 99.5% docetaxel with a mean particle size (number) of 0.915 microns, a SSA of 33.4 $mg^2/g$, and a bulk density (not tapped) of 0.0675 $g/cm^3$ used in this example) in Suspension, 10 mg/mL.

Abraxane® diluted to 6 mg/mL.

Paclitaxel solution for injection diluted to 6 mg/mL.

Docetaxel solution for injection diluted to 10 mg/mL.

Epithelial membrane substrates: Porcine bladder and porcine intestine were sourced. Upon receipt of the bladder and intestine, the membranes were stored at −20° C. until used. Prior to use, the membranes were removed from the freezer and allowed to thaw fully at ambient temperature.

Equipment:

Franz-type Diffusion Cells (FDCs): 64 diffusion cells with 3.3 ml receptor volume and a 0.55 cm2 receptor fluid exposure surface area.

Stirring Dry Block Heaters: Reacti-Therm #18823 stirring dry block heaters were used to maintain the receptor fluid at 32±0.5° C. with constant stirring throughout the study.

Agilent 1260 HPLC unit with a G16120 MS detector, ID#: TM-EQ-069.

Receptor Fluid: The receptor fluid consisted of 60 vol %/40 vol % methanol/water at pH 4 with 0.01 wt % $NaN_3$ (added as a preservative). The solubility of paclitaxel and docetaxel in the Receptor Fluid was determined to be sufficient to maintain sink conditions throughout the study. After mixing and degassing the Receptor Fluid it was filtered through a ZapCapCR 0.2 µm membrane under vacuum; the Receptor Fluid, so filtered, was stirred for an additional 20 minutes under vacuum.

Experimental Procedure:
1. The receptor wells were filled with degassed Receptor Fluid using a pipette.
2. A 6 mm by 3 mm diameter Teflon coated magnetic stir bar was introduced into each receptor well.
3. The defrosted and washed bladder or intestine pieces were examined and only areas of even thickness and with no visible surface damage were used.
4. The bladder and intestine pieces were cut into approximately 2 cm×2 cm squares using skin scissors. The square sizes were adjusted as necessary according to the shape and dimensions of the substrate, but were selected to be approximately uniform in size among all FDCs.
5. Substrate pieces were centered on each inverted donor compartment.
6. The donor and receptor well compartments were then aligned and clamped together with a pinch clamp, ensuring that the substrate pieces were centered between both donor and receptor wells.
7. Additional Receptor Fluid was added as necessary. Air bubbles in the receptor well, if any, were removed by tilting the FDC assembly such that the air escapes along the sample port. Receptor wells were filled with approximately 3.3 ml of Receptor Fluid.
8. The assembled FDCs were placed into stirring dry block heaters which were preheated to 32° C.. The Receptor Fluid was continuously agitated via the magnetic stir bar.
9. After 20 minutes, the surface of the membranes in each FDC was examined If the membranes appeared wet or showed signs of bring compromised, the cell was discarded.

Test Article Application Procedure: After the membrane integrity tests were complete and the cells appropriately sorted, samples of the test articles were then applied to the surface of the substrate. A one-time dosing regimen was used for this study. For all formulations, 100 µl of the formulation was introduced into the donor cells. The donor cells were then capped for the remainder of the experiment. For NanoPac suspension, Paclitaxel solution for injection, and Abraxane, the amount of paclitaxel drug active corresponded to 0.6 wt % correlating to a dose of 1091 µg/cm$^2$. For NanoDoce suspension and docetaxel solution for injection, the amount of docetaxel drug active corresponded to 1.0 wt % correlating to a dose of 1818 µg/cm$^2$. "Blank" undosed FDC cells were also set up to test for background signal noise. The background noise measured from these "blank" ceils was negligible.

Sampling of Receptor Fluid: Using a graduated Hamilton type injector syringe, a 300 µl aliquot was abstracted from the sampling port of each FDC at each of 1, 3, 8, and 24 and 47 hours. Fresh Receptor Fluid was added to each receptor well to replace the volume of fluid abstracted. Each abstracted aliquot was introduced into a well in a 96-well microtiter plate. Samples were stored in a refrigerator at 4-8° C. prior to MS analysis. Samples were analyzed within 5 days of collection.

Analysis of Sample: The samples abstracted from the receptor wells were then analyzed using a MS method. The concentrations of the Active were assayed and reported in each case. After the MS testing was complete, the samples were analyzed using Chemstation software. The AUCs of the paclitaxel or docetaxel peaks were recorded and converted to µg/ml values using a calibration curve developed from the calibration standards' AUC values and known concentration values. These µg/ml values were imported into the study results Excel workbook. These concentrations were then multiplied by the receptor volume (3.3 mL) and divided by the surface area of the skin exposed to the receptor fluid (0.55 cm$^2$) for an end cumulative amount in µg/cm$^2$. For receptor fluid time points greater than 1 hr, this µg/cm$^2$ value was corrected for the sample aliquot volumes which were removed to compensate for the dilution caused by replacing the sample volume with fresh buffer solution. As an example, for the second lime point at 3 hrs, the dilution factor (300 µl aliquot/3.3 ml receptor volume or 1/11) is multiplied by the µg/cm$^2$ value calculated for the 1 hr time point, the result of which is then added to the µg/cm$^2$ concentration which is calculated using the 3 hr AUC value.

Results: The results are shown in FIG. 1, FIG. 2, and FIG. 3.

FIG. 1 is a graph of the flux of paclitaxel (delivered dose of paclitaxel active drug across a porcine bladder membrane over time) from various paclitaxel formulations.

Figure 2:
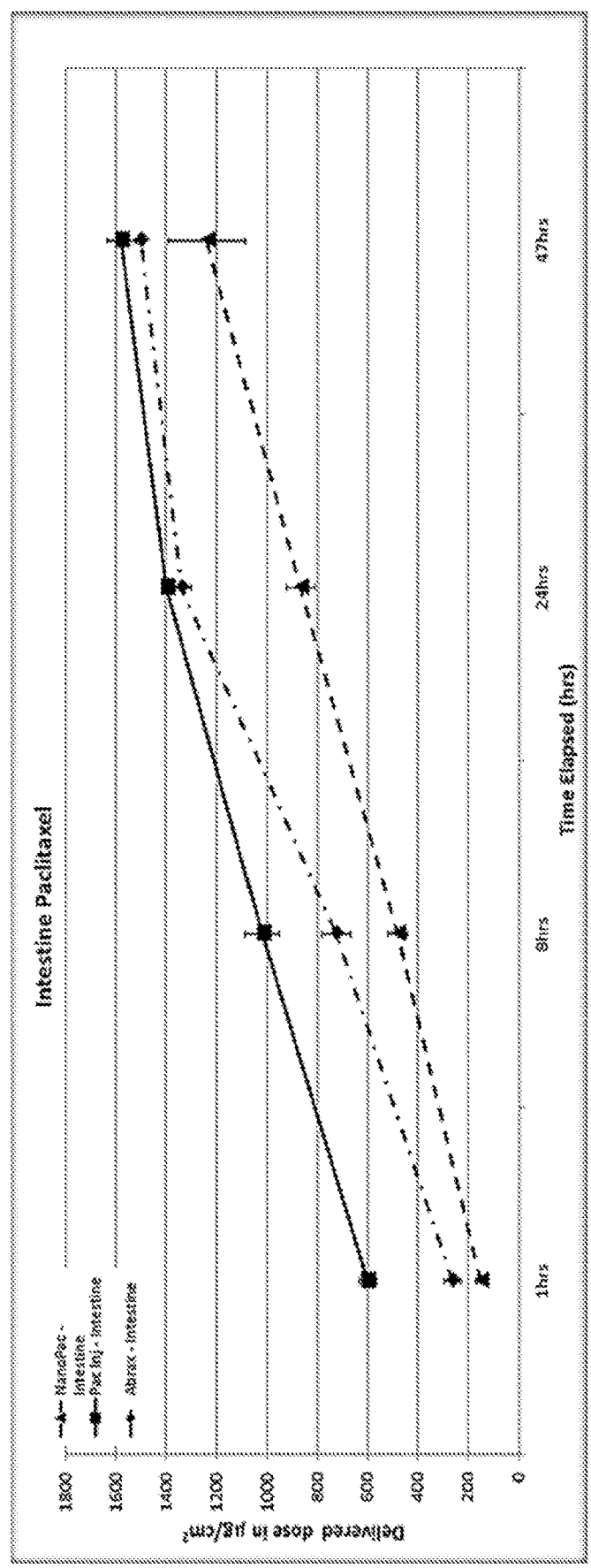
FIG. 2 is a graph of the flux of paclitaxel (delivered dose of paclitaxel active drug across a porcine intestinal membrane over time) from various paclitaxel formulations.

FIG. 2 is a graph of the flux of paclitaxel (delivered dose of paclitaxel active drug across a porcine intestinal membrane over time) from various paclitaxel formulations. Note: flux amounts greater than dose amounts were attributable to evaporation of the receptor fluid.

Figure 3:
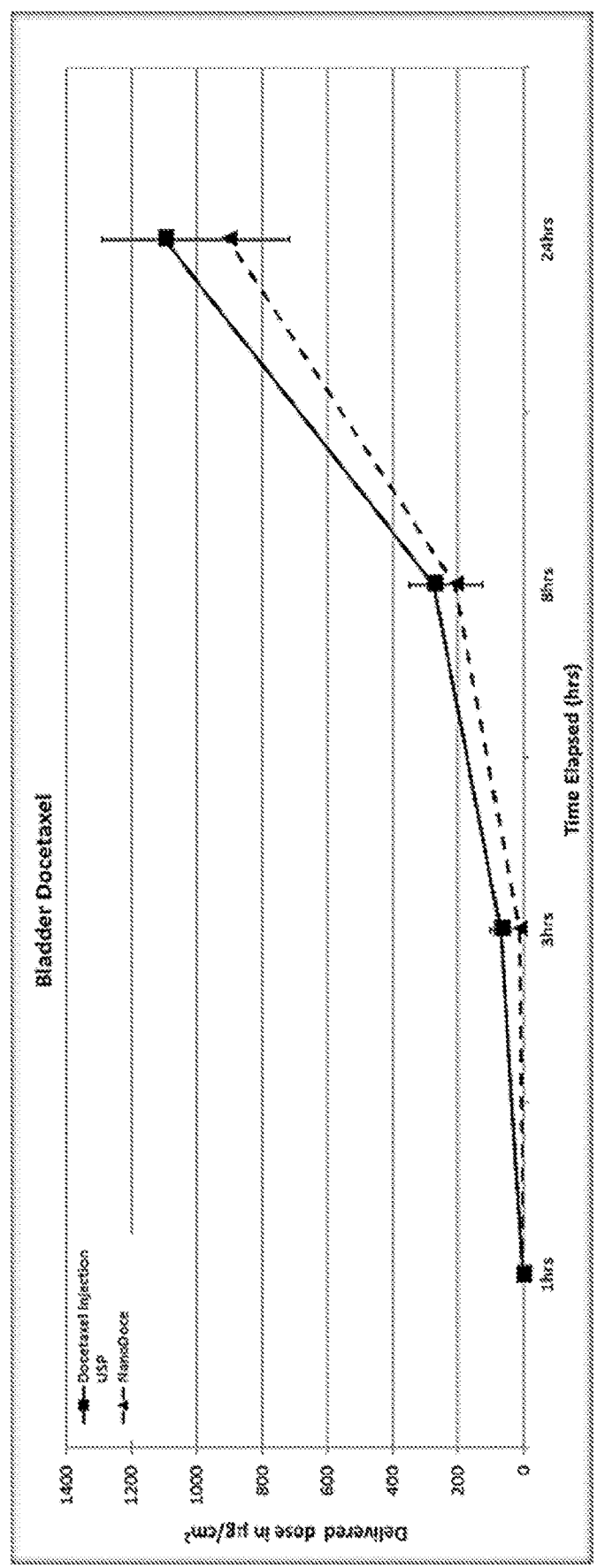
FIG. 3 is a graph of the flux of docetaxel (delivered dose of docetaxel active drug across a porcine bladder membrane over time) from various docetaxel formulations.

FIG. 3 is a graph of the flux of docetaxel (delivered dose of docetaxel active drug across a porcine bladder membrane over time) from various docetaxel formulations. Note: the 48-hour timepoint was discarded due to evaporation issues with the receptor fluid samples.

As can be seen in the figures, the NanoPac and NanoDoce formulations had the lowest flux across the membranes as indicated by the least amount of active drug delivered over time through the membranes. These results indicate that NanoPac is retained on one side of an epithelial membrane in greater amounts than Abraxane or paclitaxel solution over time. Also, NanoDoce is retained on one side of an epithelial membrane in greater amounts than docetaxel solution over time. This would suggest that NanoPac when injected into an epithelial cyst would reside within the cyst in greater amounts over time than would Abraxane or paclitaxel solution, and that NanoDoce when injected into an epithelial cyst would reside in the cyst in greater amounts over time than would docetaxel solution.

REFERENCES

ABRAXANE Package Insert. Celgene Company. Rev July 2015.
Allen, P. J., & Brennan, M. F. The management of cystic lesions of the pancreas. Adv Surg. 2007;41:211-228.
Ashgate Handbook of Antineoplastic Agents, Gower Publishing Limited, 2000.
Atar, M. et al., EUS Guided Injection of Albumin Bound Paclitaxel into Mucinous Pancreatic Cysts. Gastrointestinal Endoscopy, 81(5), AB555.
DeWitt, J., McGreevy, K., Schmidt, C. M., & Brugge, W. R. EUS-guided ethanol versus saline solution lavage for pancreatic cysts: a randomized, double-blind study. Gastrointest Endosc. 2009;70(4):710-723.
DeWitt, J. M., Al-Haddad, M., Sherman. S., LeBlanc, J., Schmidt, C. M., Sandrasegaran, K., et al. Alterations in cyst fluid genetics following endoscopic ultrasound-guided pancreatic cyst ablation with ethanol and paclitaxel. Endosc. 2014;46(06):457-464.
Farrell, J. J. Prevalence, diagnosis and management of pancreatic cystic neoplasms: current status and future directions. Gut Liver. 2015;9(5):571-589.
Farrell, J. J., Fernández-del Castillo, C. Pancreatic Cystic Neoplasms: Management and Unanswered Questions. Gastroenterology. 2013;144.1303-1315.
Fernández-del Castillo, C. & Warshaw, A. L. Cystic tumors of the pancreas. Surg Clin N Am. 1995;75(5):1001.
Ferrone, C. R., Correa-Gallego, C., Warshaw, A. L., Brugge. W. R., Forcione. D. G., Thayer, S. P., et al. Current trends in pancreatic cystic neoplasms. Arch Surg. 2009; 144(5): 448-454.
Gómez, V., Takahashi, N., Levy, M. J., McGee, K. P., Jones. A., Huang, Y., et al. EUS-guided ethanol lavage does not reliably ablate pancreatic cystic neoplasms (with video). Gastrointest endosc. 2016;83(5):914-920.
Greer, J. B., & Ferrone. C. R. Spectrum and classification of cystic neoplasms of the pancreas. Surg Oncol Clin N Am. 2016;25(2)339-350.
Jani, N., Bani Hani, M., Schulick, R. D., Hruban, R. H., & Cunningham, S. C. Diagnosis and management of cystic lesions of the pancreas. Diagn Ther Endosc. 2011:1-10.
Kirtane, T., & Bhutani, M. S. EUS for pancreatic cystic neoplasms: The roadmap to the future is much more than just a few shades of gray. Asian Pac J Trap Med. 2016: 9(12):1218-1221.
McGrath, K. Management of incidental pancreatic cysts: which guidelines? Endoscopy International Open. 2017; 05:E209-E211.
Mills, K. M., Johnson, D. M., Middlebrooks, M., & Burton, G. V. Possible Drug-Associated Pancreatitis after Paclitaxel-Cremophor Administration. Pharmacother: J Human Pharmacol Drug Ther. 2000;20(1):95-97.
Moyer, M. T., Dye, C. E., Sharzehi, S., Ancrile, B., Mathew, A., McGarrity, T. J., et al. Is alcohol required for effective pancreatic cyst ablation? The prospective randomized CHARM trial pilot study. Endosc Int Open, 2016;4(05): E603-E607.
Muthusamy, V. R., Chandrasekhara. V., Acosta, R. D., Bruining, D. H., Chathadi. K. V., Eloubeidi, M. A., et al. The role of endoscopy in the diagnosis and treatment of cystic pancreatic neoplasms. Gastrointest Endosc, 2016; 83(3):481-488.
National Cancer Institute (2016). SEER Stat Fact Sheets: Pancreas Cancer http://seer.cancer.gov/statfacts/html/pancreas.html Accessed Sep. 13, 2016.
Oh, H. C., Seo, D. W., Lee, T. Y., Kim, J. Y., Lee, S. S., Lee, S. K., et al. New treatment for cystic tumors of the pancreas: EUS-guided ethanol lavage with paclitaxel injection. Gastrointest Endosc. 2008;67(4):636-642.
Oh, H. C., Seo, D. W., Kim, S. C., Yu, E., Kim, K., Moon, S. H., et al. Septated cystic tumors of the pancreas: is it possible to treat them by endoscopic ultrasonography-guided intervention? Scand J Gastroenterol. 2009;44(2): 242-247.
Oh, H. C., Seo, D. W., Song. T. J., Moon, S. R, Park, D. H., Lee, S. S., et al. Endoscopic ultrasonography-guided ethanol lavage with paclitaxel injection treats patients with pancreatic cysts. Gastroenterol. 2011;140(1):172-179.
Pitman, M. B., Lewandrowski, K., Shen, J., Sahani, D., Brugge, W., & Fernandez-del Castillo, C. Pancreatic cysts. Cancer Cytopath. 2010;118(1);1-13.
Rheology Modifiers Handbook—Practical Use and Application, Braun, William Andrew Publishing, 2000.
Sarr, M. G., Carpenter, H. A., Prabhakar, L. P. Orchard, T. F., Hughes, S., van Heerden, J. A., et al. Clinical and Pathologic Correlation of 84 Mucinous Cystic Neoplasms of the Pancreas: Can One Reliably Differentiate Benign From Malignant (or Premalignant) Neoplasms?. Ann Surg. 2000;231(2):205-212.
Tamirisa, N. P., Parmar, A. D., Vargas, G. M., Mehta, H. B., Kilbane, E. M., Hall, B. L., et al. Relative contributions of complications and failure to rescue on mortality in older patients undergoing pancreatectomy. Ann Surg. 2016;263 (2):385-391.
Tanaka, M. Current best practice and controversies in the follow up of patients with asymptomatic branch duct IPMN of the pancreas HPB 2016, 18, 709-711.
Tanaka, M., et al., International consensus guidelines 2012 for the management of IPMN and MCN of the pancreas. Pancreatology. 12 (2012) 183-197.
Tanaka, M., et al., Clinical aspects of intraductal papillary mucinous neoplasm of the pancreas J Gastroenterol. 2005; 40:669-675.
Tanaka, M., Chari, S., Adsay, V., Fernandez-del Castillo, C., Falconi, M., Shimizu, M., et al. International consensus guidelines for management of intraductal papillary mucinous neoplasms and mucinous cystic neoplasms of the pancreas. Pancreatol. 2006;6(1-2):17-32.

The invention claimed is:

1. A method for treating a benign epithelial cyst, the method comprising injecting a composition comprising an effective amount of paclitaxel particles and an aqueous liquid carrier directly into the benign epithelial cyst, thereby treating the benign epithelial cyst,
   wherein the paclitaxel particles comprise at least 95% of the paclitaxel,
   wherein the paclitaxel particles have a specific surface area (SSA) of at least 18 m$^2$/g,
   wherein the paclitaxel particles have a mean particle size (number) of from 0.1 microns to 5 microns,
   wherein the composition comprises a suspension of the paclitaxel particles dispersed in the carrier, and
   wherein the composition does not contain ethanol.

2. The method of claim 1, wherein the carrier comprises 0.9% saline solution.

3. The method of claim 1, wherein the carrier comprises a surfactant.

4. The method of claim 3, wherein the surfactant is a polysorbate.

5. The method of claim 4, wherein the polysorbate is polysorbate 80, and wherein the polysorbate 80 is present in the aqueous carrier at a concentration of between about 0.01% v/v and about 1% v/v.

6. The method of claim 1, wherein the composition further comprises a diluent, wherein the carrier and the diluent form a mixture, and wherein the composition is a suspension of the paclitaxel particles dispersed in the carrier/diluent mixture.

7. The method of claim 6, wherein the diluent comprises 0.9% saline solution.

8. The method of claim 1, wherein the paclitaxel particles have a bulk density (not tapped) of 0.05 g/cm$^3$ to 0.15 g/cm$^3$.

9. The method of claim 1, wherein the concentration of the paclitaxel particles in the composition is between about 6 mg/mL and about 15 mg/mL.

10. The method of claim 1, wherein the paclitaxel particles have a mean particle size (number) of from 0.1 microns to 1.5 microns.

11. The method of claim 1, wherein the paclitaxel particles are crystalline particles.

12. The method of claim 1, wherein the composition and paclitaxel particles exclude albumin.

13. The method of claim 1, wherein cyst fluid is withdrawn from the benign epithelial cyst prior to injecting the composition.

14. The method of claim 13, wherein the volume of the composition injected into the benign epithelial cyst is equal to the volume of cyst fluid removed from the benign epithelial cyst.

15. The method of claim 1, wherein the benign epithelial cyst is a benign pancreatic cyst.

16. The method of claim 15, wherein the benign pancreatic cyst is a benign mucinous pancreatic cyst.

17. The method of claim 1, wherein the injection of the composition is conducted by endoscopic ultrasound-guided fine needle injection (EUS-FNI).

18. The method of claim 1, wherein the benign epithelial cyst is reduced in volume/size, is eliminated, or is ablated after injection of the composition, and/or wherein pain associated with the benign epithelial cyst is reduced.

\* \* \* \* \*

UNITED STATES PATENT AND TRADEMARK OFFICE
CERTIFICATE OF CORRECTION

| | | |
|---|---|---|
| PATENT NO. | : 11,523,983 B2 | Page 1 of 1 |
| APPLICATION NO. | : 17/315804 | |
| DATED | : December 13, 2022 | |
| INVENTOR(S) | : diZerega et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 51 days.

Signed and Sealed this
Twenty-first Day of January, 2025

Coke Morgan Stewart
*Acting Director of the United States Patent and Trademark Office*